United States Patent
Hudson et al.

(10) Patent No.: US 11,988,670 B2
(45) Date of Patent: *May 21, 2024

(54) INTEGRATED SAMPLE PROCESSING SYSTEM WITH MULTIPLE DETECTION CAPABILITY

(71) Applicants: BECKMAN COULTER, INC., Brea, CA (US); DH TECHNOLOGIES DEVELOPMENT PTE. LTD., Singapore (SG)

(72) Inventors: Aaron Hudson, Northborough, MA (US); Takayuki Mizutani, Edina, MN (US); Subhasish Purkayastha, Acton, MA (US); Thomas W. Roscoe, Prior Lake, MN (US)

(73) Assignees: Beckman Coulter, Inc., Brea, CA (US); DH Technologies Development Pte. Ltd. (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/814,530

(22) Filed: Jul. 25, 2022

(65) Prior Publication Data
US 2023/0011115 A1    Jan. 12, 2023

Related U.S. Application Data

(63) Continuation of application No. 16/616,052, filed as application No. PCT/US2018/033927 on May 22, 2018, now Pat. No. 11,402,386.
(Continued)

(51) Int. Cl.
G01N 33/68    (2006.01)
G01N 27/624   (2021.01)
(Continued)

(52) U.S. Cl.
CPC ....... *G01N 33/6848* (2013.01); *G01N 27/624* (2013.01); *H01J 49/0031* (2013.01); *H01J 49/0036* (2013.01); *H01J 49/025* (2013.01)

(58) Field of Classification Search
CPC .............. G01N 33/6848; G01N 27/624; H01J 49/0031; H01J 49/0036; H01J 49/025
See application file for complete search history.

(56) References Cited

U.S. PATENT DOCUMENTS 10,088,460 B2 *  10/2018  DeWitte ............ G01N 30/7233
11,402,386 B2 *  8/2022  Hudson ................... H01J 49/04
2011/0287446 A1  11/2011  Kanda et al.

FOREIGN PATENT DOCUMENTS

JP    2007-000687    1/2007
JP    2010-175355    8/2010
(Continued)

OTHER PUBLICATIONS

Japan Patent Office, Office Action regarding Serial No. 2019-564473, 5 pages, dated Apr. 13, 2022.
(Continued)

*Primary Examiner* — Nicole M Ippolito
*Assistant Examiner* — Hanway Chang
(74) *Attorney, Agent, or Firm* — McAndrews, Held & Malloy, Ltd.

(57) ABSTRACT

An integrated sample processing system including an analyzer and a mass spectrometer is disclosed. The integrated sample processing system can perform multiple different types of detection, thereby providing improved flexibility and better accuracy in processing samples. The detection systems in the sample processing system may include an optical detection system and a mass spectrometer.

19 Claims, 15 Drawing Sheets

Related U.S. Application Data

(60) Provisional application No. 62/607,773, filed on Dec. 19, 2017, provisional application No. 62/509,601, filed on May 22, 2017.

(51) Int. Cl.
  *H01J 49/00* (2006.01)
  *H01J 49/02* (2006.01)

(56) References Cited

FOREIGN PATENT DOCUMENTS

| JP | 2016-156675 | 9/2016 |
|---|---|---|
| WO | 2016006398 A1 | 1/2016 |

OTHER PUBLICATIONS

Gaelle Bridon, et al.: "Improvement of Phosphoproteome Analyses Using FAIMS and Decision Tree Fragmentation. Application to the Insulin Signaling Pathway in *Drosophila melanogaster* S2 Cells," Journal of Proteome Research, American Chemical Society, pp. 927-940, dated Nov. 7, 2011.

Japan Patent Office, Japanese Publication for Opposition No. 58-000628, 3 pages, dated Apr. 13, 2022.

PCT, "International Search Report," regarding Application No. PCT/US2018/033927, 13 pages, mailed Oct. 5, 2018.

EPO, "Communication pursuant to Article 94(3) EPC," 5 pages, dated Jun. 5, 2022.

* cited by examiner

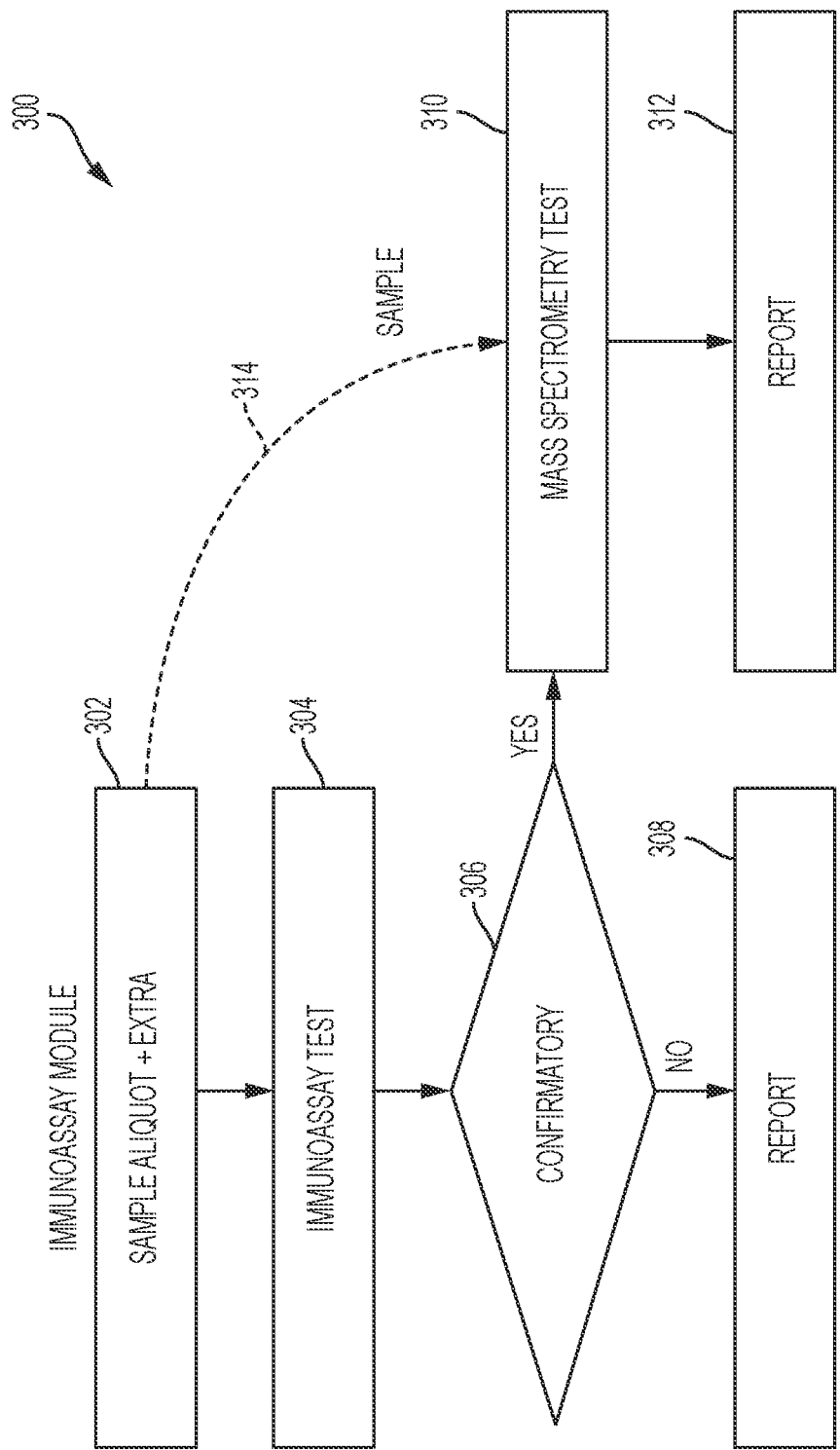

INTEGRATED SAMPLE PROCESSING SYSTEM WITH MULTIPLE DETECTION CAPABILITY

CROSS-REFERENCES TO RELATED APPLICATIONS

This application is a continuation of the U.S. patent application Ser. No. 16/616,052, filed on Nov. 22, 2019, which is a § 371 national stage entry of International Patent Application No. PCT/US2018/033927, filed on May 22, 2018, which claims the benefit of U.S. Provisional Patent Application No. 62/509,601, filed on May 22, 2017, and U.S. Provisional Patent Application No. 62/607,773, filed on Dec. 19, 2017, all of which are hereby incorporated by reference in their entireties for all purposes.

BACKGROUND

Mass Spectrometry (MS) is an analytical technique used for determining the elemental composition of samples, quantifying the mass of particles and molecules, and elucidating the chemical structure of molecules. Various types of MS with high specificity, such as Liquid Chromatography (LC-MS), Gas Chromatography (GC-MS), and Matrix-Assisted Laser Desorption/Ionization/Time-Of-Flight (MALDI-TOF MS), are being increasingly being used in clinical diagnostics. These MS techniques overcome many of the limitations of immunoassays (e.g. non-specific binding and cross reactivity of analytes) and offer many advantages).

To date, MS techniques have not found widespread clinical application due to challenges including sample preparation, online extraction, throughput, automation, laboratory information system interfacing, inter-instruments standardization and harmonization.

Embodiments of the invention address these and other challenges, individually and collectively.

BRIEF SUMMARY

Some embodiments of the invention may include an integrated sample processing system that may include an analyzer such as a chemical analyzer or an immunoanalyzer that is integrated with a mass spectrometer. Embodiments of the invention provide the advantage of having a common sample preparation station, with the option to use multiple detection systems. Such detection systems may include the mass spectrometer and an optical detection system that may be present in the analyzer. The optical detection system may operate using immunoassay detection processes such as chemiluminescence or fluorescence.

Embodiments of the invention can also include mass spectrometric systems and methods for analyzing small and large molecules (proteins). In some embodiments, the workflow from sample preparation to detection is simplified relative to conventional sample preparation methods. In the simplified sample preparation methods according to embodiments of the invention, there is no need to use a centrifugation system and or an LC system. Eliminating centrifuges and LC systems in a sample processing system reduces the complexity and improves the robustness of an overall sample analysis process, improves the TAT (turn-around time) of the samples being processed, and/or improves or maintains the accuracy of the analyses of the samples being processed.

One embodiment of the invention is directed to a sample processing system comprising: an analyzer comprising (i) a sample presentment unit configured to hold a plurality of sample tubes containing samples; (ii) an aliquoting station comprising a pipettor and configured to provide an aliquot of a sample in a sample tube in the plurality of sample tubes to a reaction vessel, and (iii) an optical detection station configured to detect the analyte in a first processed sample aliquot of the sample in the reaction vessel using the pipettor. A mass spectrometer can be coupled to the analyzer. The mass spectrometer is configured to receive a second processed sample aliquot from the analyzer and detect the analyte in the received second processed sample aliquot. The sample processing system can include a control system configured to control the analyzer and the mass spectrometer.

Another embodiment of the invention is directed to a method performed by a sample processing system comprising an analyzer comprising an aliquotting station comprising at least one pipettor, a mass spectrometer, a sample introduction apparatus, and a control system. The control system can be operatively coupled to the analyzer, the mass spectrometer, and the sample introduction apparatus. The method comprises: providing, by the at least one pipettor of the aliquoting station, a first sample aliquot of a sample, and a second sample aliquot of the sample; processing, by a plurality of processing apparatuses in the analyzer, the first sample aliquot of a sample to form a first processed sample aliquot; processing, by the plurality of processing apparatuses in the analyzer, the second sample aliquot of the sample to form a second processed sample aliquot; performing, by the analyzer, a process for detecting an analyte in the first processed sample aliquot using the immunoanalyzer; transferring, by the sample introduction apparatus, the second processed sample aliquot from the analyzer to the mass spectrometer; and detecting the analyte or another analyte in the second processed sample aliquot using the mass spectrometer.

Another embodiment of the invention is directed to a method performed by a sample processing system comprising an analyzer comprising an aliquoting station comprising at least one pipettor, a mass spectrometer, a sample introduction apparatus, and a control system, the control system operatively coupled to the analyzer, the mass spectrometer, the sample introduction apparatus, and the control system. The method comprises: providing, by the at least one pipettor of the aliquoting station, a first sample aliquot of a sample, and a second sample aliquot of the sample; performing, by the analyzer, a primary analysis of an analyte in a first processed sample aliquot derived from a first sample aliquot of a sample in a reaction vessel; transferring, by the sample introduction apparatus, a second processed sample aliquot derived from a second sample aliquot of the sample from the analyzer to the mass spectrometer; and performing, by a mass spectrometer, a secondary analysis of the analyte or another analyte in the second processed sample aliquot in a secondary analysis.

Another embodiment of the invention is directed to a sample processing system comprising: an analyzer comprising an aliquoting station; a mass spectrometer coupled to the analyzer; a sample introduction apparatus coupled to the analyzer and the mass spectrometer; and a control system coupled to the analyzer, the mass spectrometer, and the sample introduction apparatus, where the control system comprising a processor and a computer readable medium. The computer readable medium comprising code executable by the processor to implement a method comprising: directing, the aliquoting station comprising at least one pipettor, to provide a first sample aliquot of a sample, and a second sample aliquot of the sample; directing the analyzer to process a reaction vessel containing the first sample aliquot of a sample to form a first processed sample aliquot; directing the analyzer to perform a primary analysis of an analyte in the first processed sample aliquot; directing the analyzer to process the second aliquot of the sample to form a second processed sample aliquot; directing the sample introduction apparatus to transfer the second processed sample aliquot of the sample from the analyzer to the mass spectrometer; and directing the mass spectrometer to perform a secondary analysis of the analyte or another analyte in the second processed sample aliquot.

Another embodiment of the invention is directed to a method of performing an analysis, the method being performed by a sample processing system comprising an analyzer, a mass spectrometer, a sample introduction apparatus, and a control system, the control system operatively coupled to the analyzer, the mass spectrometer, the sample introduction apparatus, and the control system. The method comprises: performing, by the analyzer, a primary analysis for a first biomarker of a disease in a first processed sample aliquot derived from a first sample aliquot of a sample in a reaction vessel; transferring, by the sample introduction apparatus, a second processed sample aliquot derived from a second sample aliquot of the sample from the analyzer to the mass spectrometer; and performing, by a mass spectrometer, a secondary analysis for a second biomarker of said disease in the second processed sample aliquot in a secondary analysis.

Another embodiment of the invention is directed to a sample processing system comprising: an analyzer comprising (i) a sample presentment unit configured to hold a plurality of sample tubes containing samples; (ii) an aliquoting station configured to provide a first aliquot of a sample comprising an analyte in a sample tube in the plurality of sample tubes to a reaction vessel, and a second aliquot, and (iii) an optical detection station configured to detect the analyte in a first processed sample aliquot of the sample in the reaction vessel; a mass spectrometer coupled to the analyzer, wherein the mass spectrometer is configured to receive a second processed sample aliquot derived from the second aliquot from the analyzer and detect the analyte in the received second processed sample aliquot; and a control system configured to control the analyzer and the mass spectrometer.

Another embodiment of the invention is directed to a method performed by a sample processing system comprising an analyzer, a mass spectrometer, a sample introduction apparatus, and a control system, the control system operatively coupled to the analyzer, the mass spectrometer, the sample introduction apparatus, and the control system. The method comprises: performing, by the analyzer, a primary analysis of an analyte in a first processed sample aliquot derived from the first sample aliquot of a sample in a reaction vessel; determining, whether a concentration of analyte in the first processed sample aliquot is below, above or equal to a predetermined threshold; transferring, by the sample introduction apparatus, a second processed sample aliquot derived from the second sample aliquot of the sample from the analyzer to the mass spectrometer; and performing, by a mass spectrometer, a secondary analysis of the analyte or another analyte in the second processed sample aliquot in a secondary analysis.

Another embodiment of the invention is directed to a sample processing system comprising: an analyzer comprising (i) a sample presentment unit configured to hold a plurality of sample tubes containing samples; (ii) an aliquoting station and configured to provide an aliquot of a sample comprising an analyte in a sample tube in the plurality of sample tubes to a reaction vessel, and (iii) an optical detection station configured to detect the analyte in a first processed sample aliquot of the sample in the reaction vessel; a mass spectrometer coupled to the analyzer, wherein the mass spectrometer is configured to receive the first processed sample aliquot and/or the second processed sample aliquot from the analyzer and detect the analyte in the first processed sample aliquot and/or the second processed sample aliquot; and a control system configured to control the analyzer and the mass spectrometer. The control system comprises: a data processor; and a computer readable medium, the computer readable medium comprising code, executable by the data processor to implement a method. The method comprises: determining, using data from the optical detection station, whether detection of the analyte in the first processed sample aliquot at the optical detection station is below, above or equal to a predetermined threshold; causing, in response to determining, the analyzer to process the second sample aliquot to form the second processed sample aliquot, and the sample introduction apparatus to transfer the second processed sample aliquot from the analyzer to the mass spectrometer; and causing the mass spectrometer to detect a presence of the analyte or another analyte in the second processed sample aliquot.

Another embodiment of the invention is directed to a method performed by a sample processing system comprising at least a mass spectrometer, a sample introduction apparatus, and a control system, the control system being operatively coupled to the mass spectrometer and the sample introduction apparatus. The method comprises: performing, by the mass spectrometer, a primary analysis of an analyte from a first processed sample aliquot of a first sample aliquot of the sample; and after performing the primary analysis, performing, by the mass spectrometer or an analyzer in the sample processing system, a secondary analysis of the analyte or another analyte in a second processed sample aliquot derived from a second aliquot of the sample.

Another embodiment of the invention is directed to a sample processing system comprising: a mass spectrometer; a sample introduction apparatus; and a control system, wherein the control system controls operation of the mass spectrometer and the sample introduction apparatus, and wherein the control system comprises a processor, and a computer readable medium. The computer readable medium comprises code, executable by the processor, for implementing a method comprising: performing, by the mass spectrometer, a primary analysis of an analyte from a first processed sample aliquot of a first sample aliquot of the sample; and after performing the primary analysis, performing, by the mass spectrometer or an analyzer in the sample processing system, a secondary analysis of the analyte or another analyte in a second processed sample aliquot derived from a second aliquot of the sample.

These and other embodiments of the invention are described in further detail below, with reference to the drawings.

BRIEF DESCRIPTION OF THE DRAWINGS

FIGS. 3A and 3B show high level flowcharts illustrating processing steps performed by a sample processing system according to embodiments of the invention. The flowcharts illustrate different detection operations that can be performed in the sample processing system.

DETAILED DESCRIPTION

Figure 1:
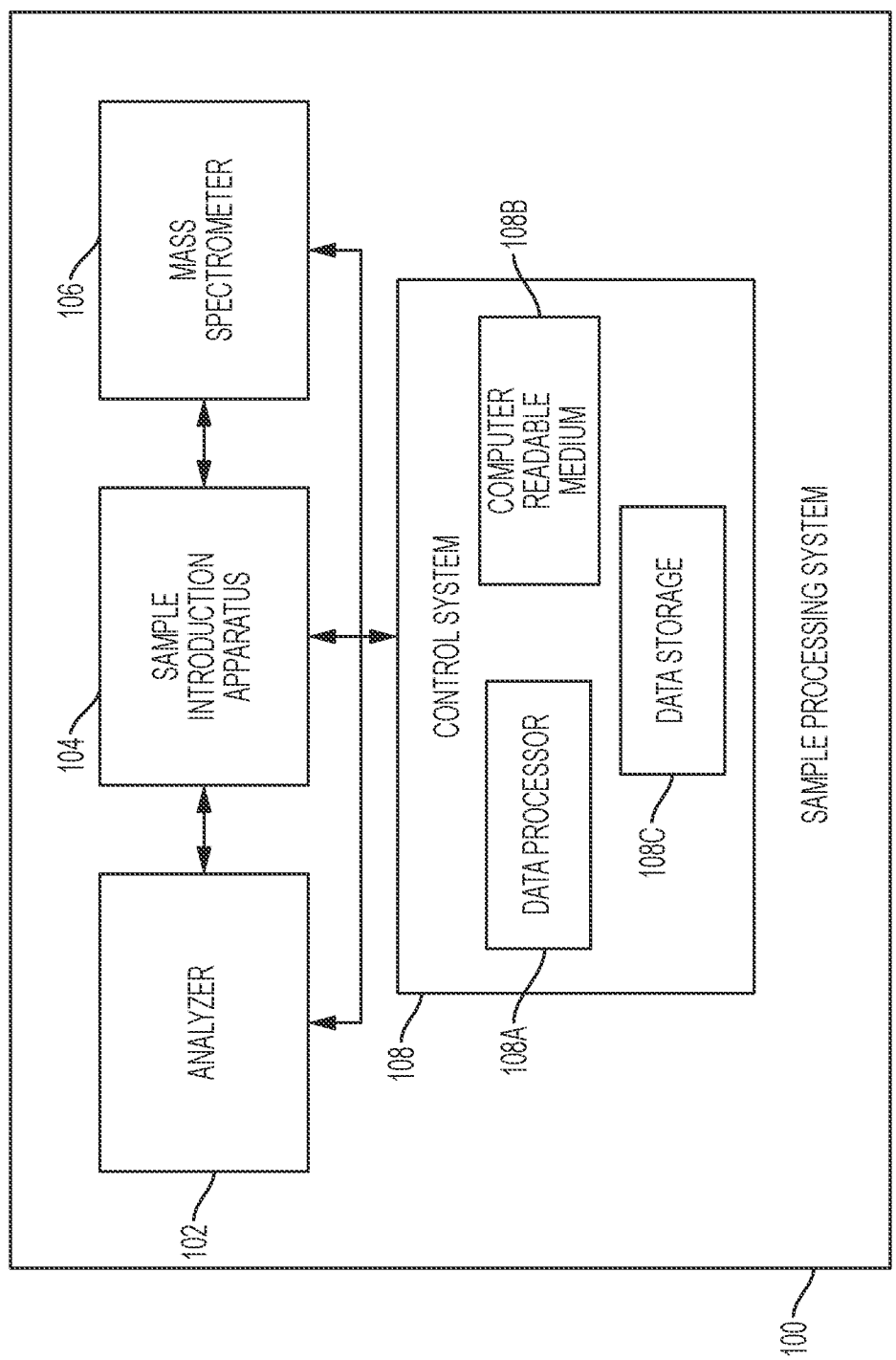
FIG. 1 shows a block diagram of an sample processing system according to an embodiment of the invention.

Embodiments of the invention may be used to detect the presence, absence, or concentration of analytes in biological or chemical samples. Biological samples such as biological fluids may include, but are not limited to, blood, plasma, serum, or other bodily fluids or excretions, such as but not limited to saliva, urine, cerebrospinal fluid, lacrimal fluid, perspiration, gastrointestinal fluid, amniotic fluid, mucosal fluid, pleural fluid, sebaceous oil, exhaled breath, and the like. Chemical samples may include any suitable types of samples including chemicals including water samples.

Prior to discussing embodiments of the invention, some terms may be described in further detail.

The term "analyzer" may include any suitable instrument that is capable of analyzing a sample such as a biological sample. Examples of analyzers include mass spectrometers, immunoanalyzers, hematology analyzers, microbiology analyzers, and/or molecular biology analyzers.

In some embodiments, the analyzer can be an immunoanalyzer (typically detecting a label (chemoluminescent, electrochemiluminescent fluorescent, radioactive, isotope, DNA, etc. or label free system). Other types of analyzers may include hematology analyzers, microbiology analyzers, chemistry analyzers, urine analyzers, biochemical analyzers, and/or a molecular biology analyzers. When analyzing a biological sample, one or more of these types of analyzers, in any suitable combination, may be used to analyze the biological sample.

A hematology analyzer can be used to perform complete blood counts, erythrocyte sedimentation rates (ESRs), and/or coagulation tests. Automated cell counters sample the blood, and quantify, classify, and describe cell populations using both electrical and optical techniques.

A microbiology analyzer can function as a diagnostic tool for determining the identity of a biological organism. In some embodiments, a microbiology analyzer can identify an infecting microorganism. Such analyzers can use biochemicals in a plurality of small sample test microwells in centrifugal rotors that contain different substrates, or in multi-well panels, depending on the type of test being performed.

A molecular biology analyzer can be a device which can analyze a biological sample at its molecular level. An example of a molecular biology analyzer may include a nucleic acid analyzer such as a DNA analyzer.

A chemistry analyzer can run assays on clinical samples such as blood serum, plasma, urine, and cerebrospinal fluid to detect the presence of analytes relating to disease or drugs. A chemistry analyzer may use photometry. In photometry, a sample is mixed with the appropriate reagent to produce a reaction that results in a color. The concentration of the analyte determines the strength of color produced. The photometer shines light of the appropriate wavelength at the sample and measures the amount of light absorbed, which is directly correlated to the concentration of the analyte in the sample. Another analytical method used in a chemistry analyzer is the use of ion selective electrodes (ISE) to measure ions such as $Na^+$, $K^+$, $Cl^-$, and $L^+$. An ISE is a sensor that determines the concentration of ions in a solution by measuring the current flow through an ion selective membrane.

The term "analyte" may include a substance whose presence, absence, or concentration is to be determined according to embodiments of the present invention. Typical analytes may include, but are not limited to organic molecules, hormones (such as thyroid hormones, estradiol, testosterone, progesterone, estrogen), metabolites (such as glucose or ethanol), proteins, lipids, carbohydrates and sugars, steroids (such as Vitamin D), peptides (such as procalcitonin), nucleic acid segments, biomarkers (pharmaceuticals such as antibiotics, benzodiazepine), drugs (such as immunosuppressant drugs, narcotics, opioids, etc.), molecules with a regulatory effect in enzymatic processes such as promoters, activators, inhibitors, or cofactors, microorganisms (such as viruses (including EBV, HPV, HIV, HCV, HBV, Influenza, Norovirus, Rotavirus, Adenovirus etc.), bacteria (*H. pylori, Streptococcus*, MRSA, C. diff, Ligionella, etc.), fungus, parasites (*plasmodium*, etc.), cells, cell components (such as cell membranes), spores, nucleic acids (such as DNA and RNA), etc. Embodiments of the invention can also allow for the simultaneous analysis of multiple analytes in the same class or different classes (e.g. simultaneous analysis of metabolites and proteins). In embodiments of the invention, the analysis of a particular analyte such as a biomarker may indicate that a particular condition (e.g., disease) is associated with a sample that contains the analyte.

The term "immunoassay" can a laboratory method used to determine the amount of an analyte in a sample. It can be based on the interaction of antibodies with antigens, and because of the degree of selectivity for the analyte (either antigen or antibody), an immunoassay can be used to quantitatively determine very low concentrations of analyte in a test sample. An "immunoanalyzer" can include an instrument on which immunoassays have been automated. Various immunoanalyzers are commercially available including the DxI™ system (Beckman Coulter, CA), the ADVIA™ and CENTAUR™ systems (Siemens Healthcare, Germany), the COBAS™ system (Roche Diagnostic, Germany), the ARCHITECT™ system (Abbott, IL), the VITROS™ system (Ortho-clinical Diagnostic, NJ), and the VIDAS™ system (Biomerieux, France).

A "mass spectrometer" is an instrument which can measure the masses and relative concentrations of atoms and molecules. One example of a mass spectrometer makes use of the basic magnetic force on a moving charged particle. Basically, the instrument ionizes a sample and then deflects the ions through a magnetic field based on the mass-to-charge ratio of the ion. The mass spectrum can then be used to determine the elemental or isotopic signature of a sample, the masses of particles and of molecules, and to elucidate the chemical structures of molecules, such as peptides and other chemical compounds. Commercially available mass spectrometers can be categorized based on how they sector mass selection, including time-of-flight, quadrupole MS, ion traps (including 3D quadrupole, cylindrical ion traps, linear quadropole ion traps, orbitraps), Fourier transform ion cyclotron resonance (FTMS), etc. Alternatively, they can be sectored based on ion source (laser desorption, matrix assisted laser desorption, thermal ionization, plasma, spark source, etc.) or detectors (electron multipliers (such as Faraday cups and ion-to-photon detectors), inductive detectors, etc.). In a preferred embodiment, the mass spectrometer can be a triple quadrupole mass spectrometer.

In the specific examples provided below, a sample processing system including an immunoanalyzer and a mass spectrometer are described in detail. However, embodiments of the invention are not limited thereto. Instead of an immunoanalyzer, another type of analyzer such as a chemistry analyzer can be used instead of the immunoanalyzer. Many of the functions and features in the immunoanalyzer may also be present in the chemistry analyzer (e.g., reagent storage, aliquoting station, sample preparation station, etc.). Further, additional components such as the sample introduction apparatus may also be used with the chemistry analyzer and the mass spectrometer in a sample processing system.

Some embodiments of the invention can include a completely integrated platform with a mass spectrometer (measuring mass) and an immunoanalyzer (typically detecting a label (chemoluminescent, electrochemiluminescent fluorescent, radioactive, isotope, DNA, etc. or label free system). The system can have at least one sample preparation station, which can be separate from or shared with the immunoanalyzer. The system can be integrated with a track system and can have the capability of (1) independent analysis by either the immunoanalyzer or mass spectrometer or (2) serial or parallel analysis by the immunoanalyzer and mass spectrometer. Serial analysis can include either retesting (e.g., same analyte tested on both analyzers) or reflex testing (e.g., a first analyte is tested on one analyzer (typically the immunoanalyzer) and a second or more analyte(s) are tested on the other analyzer (typically the mass spectrometer)).

More specifically, embodiments of the invention can include an immunoanalyzer that integrates to a mass spectrometer. A sample preparation station and a sample introduction are also present. The system also comprises a control system that can control the mass spectrometer, the immunoanalyzer, at least one sample preparation station and at least one sample introduction system.

In some cases, a single sample preparation station is used for both the immunoanalyzer and the mass spectrometer. In other embodiments, two sample preparation stations are present and can be used for exclusively or mutually by the immunoanalyzer and the mass spectrometer. The sample preparation system comprises a means for aliquotting the sample (such as an aliquotter) such as an aliquoting station comprising at least one pipettor, means for holding at least one reagent pack comprising the reagents needed for the immunoassay and/or the mass spectrometer, and a means for transferring reagent from the reagent pack to the aliquotted sample. In some embodiments, the sample preparation station comprises a means for holding at least two reagent packs (i.e. one for sample preparation for the immunoanalyzer and one for sample preparation for the mass spectrometer).

In some embodiments, the sample introduction system is fluidically linked to at least one of the sample preparation systems. The sample introduction system may include direct flow injection, the use of a trap and elute system (e.g., a trap and elute system which includes 2 pumps and a 6-port switching valve), the use of an open port apparatus such as an open port probe.

The control system can cause the sample processing system to process a primary sample and provide results regarding the presence, absence, or quantity of a particular analyte in the primary sample. The control system can further cause the sample processing system to process a second sample and provide results on regarding the presence, absence, or quantity of one or more analytes in the second sample. The first and second samples can be processed by the same instrument (an immunoanalyzer or a mass spectrometer) or by a different instruments (an immunoanalyzer and a mass spectrometer). The control system can control what reagent packs are used to process samples (e.g. if mass tags are desirable to use, the control system could direct the sample preparation system to use a first reagent pack with the first sample aliquot and a different, second reagent pack containing the mass tags with the second sample aliquot).

In some embodiments of the invention, a mass analysis can be performed after initial testing of the sample using an immunoanalyzer. That is, the mass spectrometer can be used to perform reflex testing of a sample that was previously processed by the immunoanalyzer. The systems and methods according to embodiments of the invention also provide for the ability to perform automated reflex testing based upon predetermined criteria using a control system running intelligent software. Based on whether the results from the primary immunoassay meet certain criteria, the software can determine if the sample should be retested by the immunoanalyzer or reflex tested by the mass spectrometer. Since the primary sample can still be "on-deck" in the immunoanalyzer, the sample preparation for the mass spectrometric analysis assay can be initiated if the control system determines that a retest or a reflex test is desirable or necessary. The sample processing system can advantageously have reagent cartridges for both optical detection processes and mass spectrometric processes.

In some embodiments, two or more aliquots of the primary sample can be prepared: one for an immunoassay analysis and one for a mass spectrometric analysis. In some embodiments, after eluting an analyte originally present in the primary sample from an antibody bound to a magnetic particle, the eluant containing the analyte can be characterized as a processed sample aliquot, since it is derived from an original sample aliquot. The processed sample aliquot can then be analyzed by the mass spectrometer. Primary samples and processed sample aliquots, and any additional sample aliquots can be temporarily held in a sample storage unit (optionally, a chilled unit) while the control system determines if mass spectrometric analysis is needed.

When the control system determines that a retest or reflex process is necessary or desirable, the sample needs to be processed by the mass spectrometer, either a primary sample or a processed sample aliquot can be used. A retest process may be necessary or desirable if a primary analysis is viewed by the control system or other entity as being inconclusive, inadequate by itself, or incomplete. A reflex test may be necessary or desirable if the primary analysis of a first analyte indicates that further testing of one or more other analytes is desirable.

Embodiments of the invention can provide simplified workflows from sample preparation to a final analysis result with multiple options to improve the sensitivity, specificity and accuracy of the sample analysis process. As noted above, embodiments of the invention can eliminate the need for utilizing centrifugation and/or HPLC (high pressure liquid chromatography) (i.e., using a high pressure liquid chromatography column) prior to mass spectrometer analysis. In some embodiments, no centrifuge and no HPLC apparatus is present in the sample processing system.

A first example sample preparation procedure that can be performed by the sample preparation system may include immunopurification of a target analyte from a primary sample using a monoclonal or polyclonal antibody attached to a paramagnetic particle. In an immunopurification process, after the analyte is captured by the antibody, any unbound molecules are washed away in a washing process. In a subsequent elution step, the analyte is subsequently released from the antibody using a buffer and the eluant. The eluant containing the "purified" target can be characterized as a processed sample aliquot, which is then collected and analyzed by the mass spectrometer.

The antibody that is typically used in the immunopurification process can be replaced by alternatives, e.g. aptamers, nanoparticles, binding proteins, etc. The immunocapture reagent can be designed to capture a specific analyte or a specific panel of analytes, e.g., drug panel or endocrine panel, etc. In embodiments of the invention, an MRM (multiple reaction monitoring) workflow using a triple quadrupole mass spectrometer, where specific parent to daughter ion transitions are present for each analyte, can be utilized to accurately analyze the specific analytes in the panel. In case there are no differentiating transitions in tandem mass spectrometry or $MS^2$ (typically in case of isomers or isobars), a unique transition in $MS^3$ may be utilized to differentiate between them.

In a second exemplary procedure performed in the sample preparation system, protein precipitation is used to separate proteins from small molecules. The proteins in a sample aliquot are precipitated using a precipitation reagent, after which the precipitated proteins are bound to paramagnetic beads. The proteins bound to the beads can be physically separated from a supernatant using a magnetic washing process. The supernatant liquid, which can be characterized as a processed sample aliquot, can be collected and transferred to the mass spectrometer for analysis. Drug classes for definitive or stand-alone testing can be analyzed using this workflow.

In some embodiments, mass spectrometric reagents such as mass tags (e.g., Amplifex™ mass tags) can be used during the sample preparation process to enhance signals and improve sensitivity. Mass tags are typically designed to react specifically with functional groups common to a specific class of analytes, e.g., keto functionality present in steroid class or diene functionality present in the Vitamin D class, etc. Mass tags can influence fragmentation of the molecule to yield specific fragments to provide unique transitions, which can lead to more accurate results. In some cases, the differential mobility of ions in the gas phase may also be used to separate isomeric or isobaric compounds. Reagents such as this can be used with the second sample aliquot that will be processed for a mass spectrometric analysis.

Mass tags can be designed to provide accuracy in a number of ways. First, mass tags may be used to modify the differential mobility of the tagged ions (target analyte and interfering compounds) in the gas phase and simplifying their separation based on differences in their mobility properties. Separating isomeric/isobaric compounds (referred to as interfering compounds) before detection can help to improve the accuracy of any analysis results. Second, mass tags can also provide signal enhancement of the target analyte to improve sensitivity. Third, mass tags can influence fragmentation of the tagged molecules to help differentiate analytes and interfering compounds.

In embodiments of the invention, an internal standard of the analyte(s) can be added to the sample prior to analysis by a mass spectrometer. The internal standard can be an isotopic version of the analyte(s) and can compensate for losses during the sample preparation process. The ratio of the internal standard to the analyte peak can be used for quantitation. Quantitation can be performed using an external calibration curve, if desired.

In addition, embodiments of the invention can use universal trap columns and solvents, and a universal mass spectrometry source, which can make automation less complex. A universal trap column and source can work for most assays and will not require switching between different assays. The software in the control system can indicate when the life of the universal trap column is up and needs replacement.

FIG. 1 shows a high level block diagram of a sample processing system according to an embodiment of the invention. The sample processing system 100 comprises an analyzer (e.g., an immunoanalyzer) 102, a mass spectrometer 106, and a sample introduction apparatus 104. The sample introduction apparatus 104 may be physically and/or operationally coupled to the analyzer 102 and the mass spectrometer 106, and may form a single instrument in some embodiments. The sample introduction apparatus 104 may serve to transfer processed samples or sample aliquots from the analyzer 102 to the mass spectrometer 106. For example, the sample introduction apparatus 104 can be configured to transfer a first or second processed sample aliquot from the analyzer 102 to the mass spectrometer 106.

The analyzer 102 may include a number of sample aliquot processing apparatuses to form processed sample aliquots for analysis. Such processing apparatuses may process a sample or sample aliquot in any suitable manner. Examples of sample aliquot processing apparatuses include reagent addition stations (e.g., reagent pipetting stations), sample pipetting stations, incubators, wash stations (e.g., a magnetic wash station), sample storage units, etc. The plurality of sample aliquot processing apparatuses are capable of processing the first sample aliquot to form the first processed sample aliquot, and capable of processing the second sample aliquot to form the second processed sample aliquot. A "processed sample aliquot" may include a sample aliquot that is processed any suitable number of times by any suitable number of processing apparatuses.

A control system 108 can also be present in the sample processing system 100. The control system 108 can control the analyzer 102, the sample introduction apparatus 104, and/or the mass spectrometer 106. The control system 108 may comprise a data processor 108A, and a non-transitory computer readable medium 108B and a data storage 108C coupled to the data processor 108A. The non-transitory computer readable medium 108B may comprise code, executable by the processor 108A to perform the functions described herein. The data storage 108C may store data for processing samples, sample data, or data for analyzing sample data.

The data processor 108A may include any suitable data computation device or combination of such devices. An exemplary data processor may comprise one or more microprocessors working together to accomplish a desired function. The data processor 108A may include a CPU that comprises at least one high-speed data processor adequate to execute program components for executing user and/or system-generated requests. The CPU may be a microprocessor such as AMD's Athlon, Duron and/or Opteron; IBM and/or Motorola's PowerPC; IBM's and Sony's Cell processor; Intel's Celeron, Itanium, Pentium, Xeon, and/or XScale; and/or the like processor(s).

The computer readable medium 108B and the data storage 108C may be any suitable device or devices that can store electronic data. Examples of memories may comprise one or more memory chips, disk drives, etc. Such memories may operate using any suitable electrical, optical, and/or magnetic mode of operation.

The computer readable medium 108B may comprise code, executable by the data processor 108A to perform any suitable method. For example, the computer readable medium 108B may comprise code, executable by the processor 108A, to cause the sample processing system perform a method including determining, using data from the immunoanalyzer, that a detection of the analyte in a first processed sample aliquot at the immunoanalyzer is below, above or equal to a predetermined threshold; and causing, in response to determining, the analyzer to process the second aliquot of the sample to form the second processed sample aliquot, and the sample introduction apparatus to transfer the second processed sample aliquot from the analyzer to the mass spectrometer; and causing the mass spectrometer to detect the presence of the analyte or another analyte in the second processed sample aliquot. In other embodiments, the computer readable medium 108B may comprise code, executable by the data processor 108A, to cause the sample processing system to perform a method comprising: causing the immunoanalyzer to detect the analyte in the first processed sample aliquot; and causing, the mass spectrometer to detect the analyte in the second processed sample aliquot transferred from the analyzer. In yet other embodiments of the invention, the computer readable medium 108B may comprise code, executable by the data processor 108A, to cause the sample processing system to perform a method comprising determining, using data from the immunoanalyzer, that a detection of the analyte in the first processed sample aliquot at the immunoanalyzer is below or above a predetermined threshold; and causing, in response to determining, the analyzer to process the second aliquot of the sample to form the second processed sample aliquot, and the sample introduction apparatus to transfer the second processed sample aliquot from the analyzer to the mass spectrometer; and causing the mass spectrometer to detect the presence of the analyte or another analyte in the second processed sample aliquot. In yet other embodiments of the invention, the computer readable medium 108B may comprise code, executable by the data processor 108A, to perform a method comprising: directing an aliquot station comprising at least one pipettor to provide a first sample aliquot of a sample and a second sample aliquot of the sample, directing the analyzer to process a reaction vessel containing the first sample aliquot of a sample to form a first processed sample aliquot, and the second sample aliquot of the sample to form a second processed sample aliquot; directing the analyzer to perform a primary analysis of an analyte in the first processed sample aliquot; directing the sample introduction apparatus to transfer the second processed sample aliquot of the sample from the analyzer to the mass spectrometer; and directing the mass spectrometer to perform a secondary analysis of the analyte or another analyte in the second processed sample aliquot in a second process. In yet other embodiments, the computer readable medium 108B can comprise code, executable by the data processor 108A, for implementing a method comprising: performing, by the mass spectrometer, a primary analysis of an analyte from a first processed sample aliquot of a first sample aliquot of the sample; and after performing the primary analysis, performing, by the mass spectrometer or an analyzer in the sample processing system, a secondary analysis of the analyte or another analyte in a second processed sample aliquot derived from a second aliquot of the sample When the concentration of an analyte is above, below or equal to the predetermined threshold as detected by the immunoanalyzer, retesting on the mass spectrometer could confirm and/or quantitate the amount of analyte present. The predetermined threshold can correspond to a predetermined amount or predetermined concentration of the analyte in the processed first sample aliquot. Retesting by the mass spectrometer is especially useful when the concentration of analyte in the sample is above the limit of detection but below the limit of quantitation of an immunoanalyzer. Reflexing testing by the mass spectrometer is especially useful when the amount of analyte indicates further testing of other analytes should be done (e.g. if one narcotic metabolite is found, a panel of other narcotics may be desirable to run).

Figure 2:
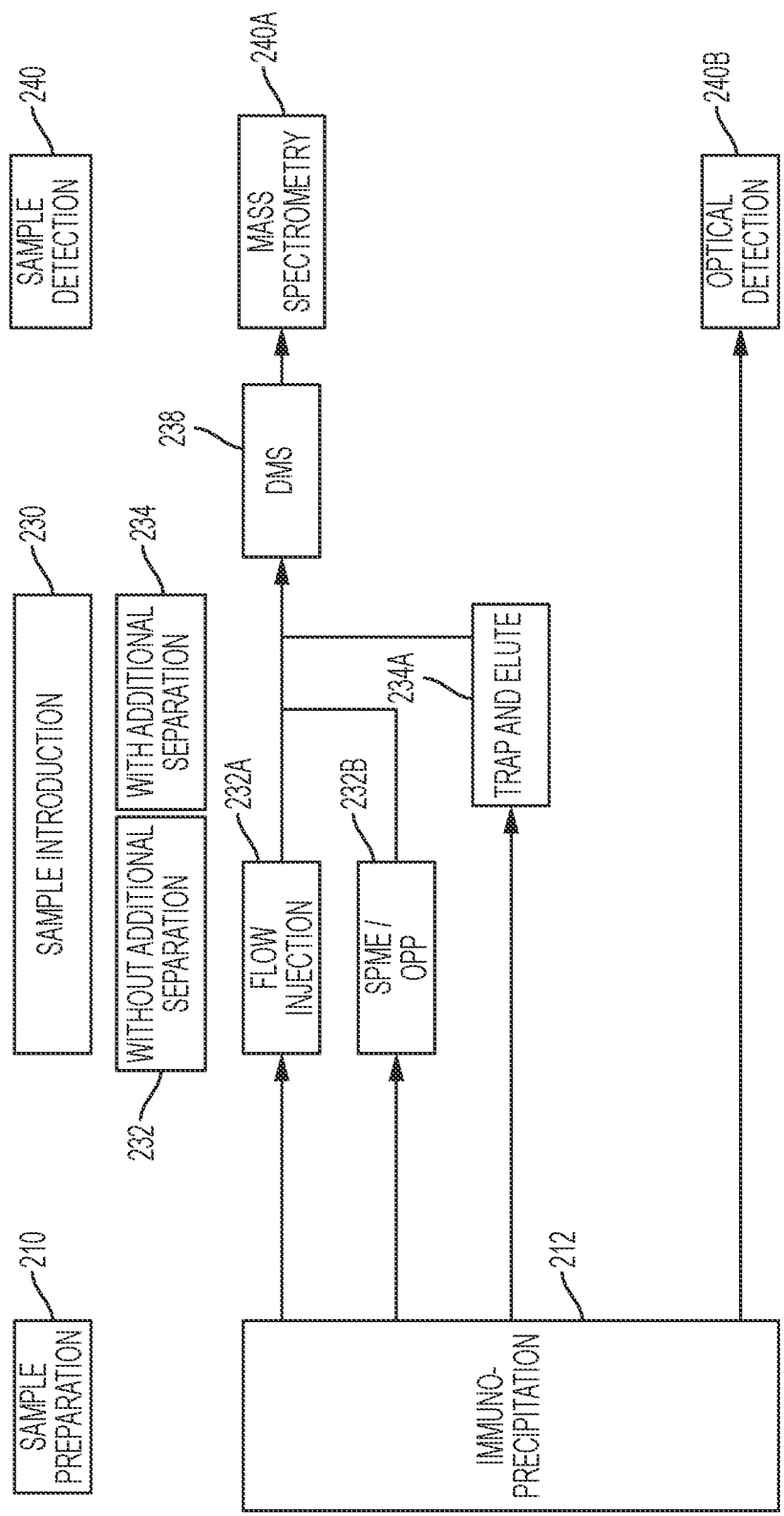
FIG. 2 shows a diagram illustrating different processing paths that can be taken in the sample processing system according to embodiments of the invention.

FIG. 2 shows a diagram illustrating different processing paths that can be taken in the sample processing system according to embodiments of the invention. A high level process flow may include a sample preparation processing module 210, a sample introduction processing module 230, and a sample detection processing module 240.

The sample preparation processing module 210 may include process steps that process a sample containing an analyte such that it may be detected during the sample detection processing module 240. In embodiments of the invention, the sample preparation processing module 210 may include an immunoprecipitation or immunopurification process. Steps in the sample preparation processing module 210 may be carried out in the analyzer 102. Steps in the sample introduction process module may be carried out in the analyzer 102, the mass spectrometer 106, or it may be a separate, stand-alone apparatus separate and apart from the analyzer 102 and the mass spectrometer 106. The sample detection process module 240 can be performed in the mass spectrometer 106 and/or an immunoanalyzer 102.

The sample introduction process module 230 includes process steps that can transfer a sample containing an analyte the analyzer 102 to the mass spectrometer 106. Also, the sample introduction process module 230 may include the transfer of a sample without additional separation 232 and with additional separation 234. Specific sample introduction processes that do not include additional separation 232 may include flow injection 232A or SPME (solid phase micro extraction)/OPP (open port probe) 232B. Sample introduction processes that can include additional separation can include a trap and elute process module 234A. An optional DMS (differential mobility spectrometry) process module 238 may be carried out downstream of the sample introduction process module 230 after the sample has been ionized but prior to the sample being mass analyzed.

The direct flow injection process module 232A may utilize an apparatus that can include a direct injection apparatus that can directly inject a processed sample from an analyzer into a mass spectromter. The apparatus may include a carrier solution source, which may be used to carry the processed sample to the mass spectrometer. A pump such as a peristalic pump may be included in the direct flow injection apparatus.

The SPME/OPP process module 232B can utilize an SPME device and an OPP apparatus, which may include an open port sampling interface. SPME can integrate sampling, sample preparation, and extraction into a single solvent-free step. Generally, an SPME device utilizes a fiber or other surface (e.g., blades, micro-tips, pins, or mesh) coated with an extracting phase to which analytes within the sample can be preferentially adsorbed when the device is inserted into a sample aliquot or processed sample aliquot. An SPME device can be proximate to an OPP, which can be a vertically aligned, co-axial tube arrangement enabling solvent delivery to a sampling end (open-port) through the tubing annulus and aspiration down the center tube into an ion source driven by a nebulizer gas.

Figure 7A:
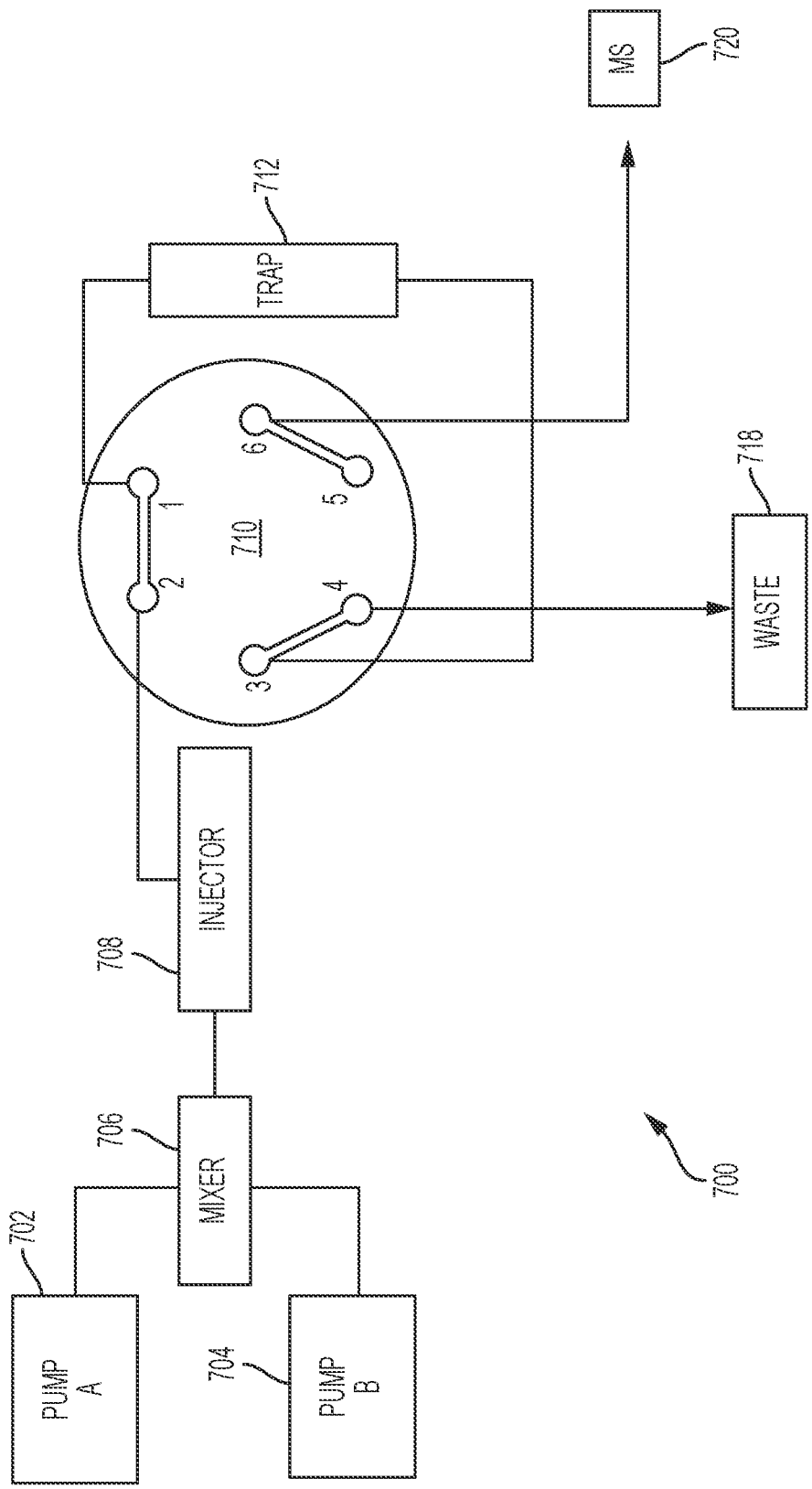
FIG. 7A shows a diagram of trap and elute system according to an embodiment of the invention in a first configuration.
Figure 7B:
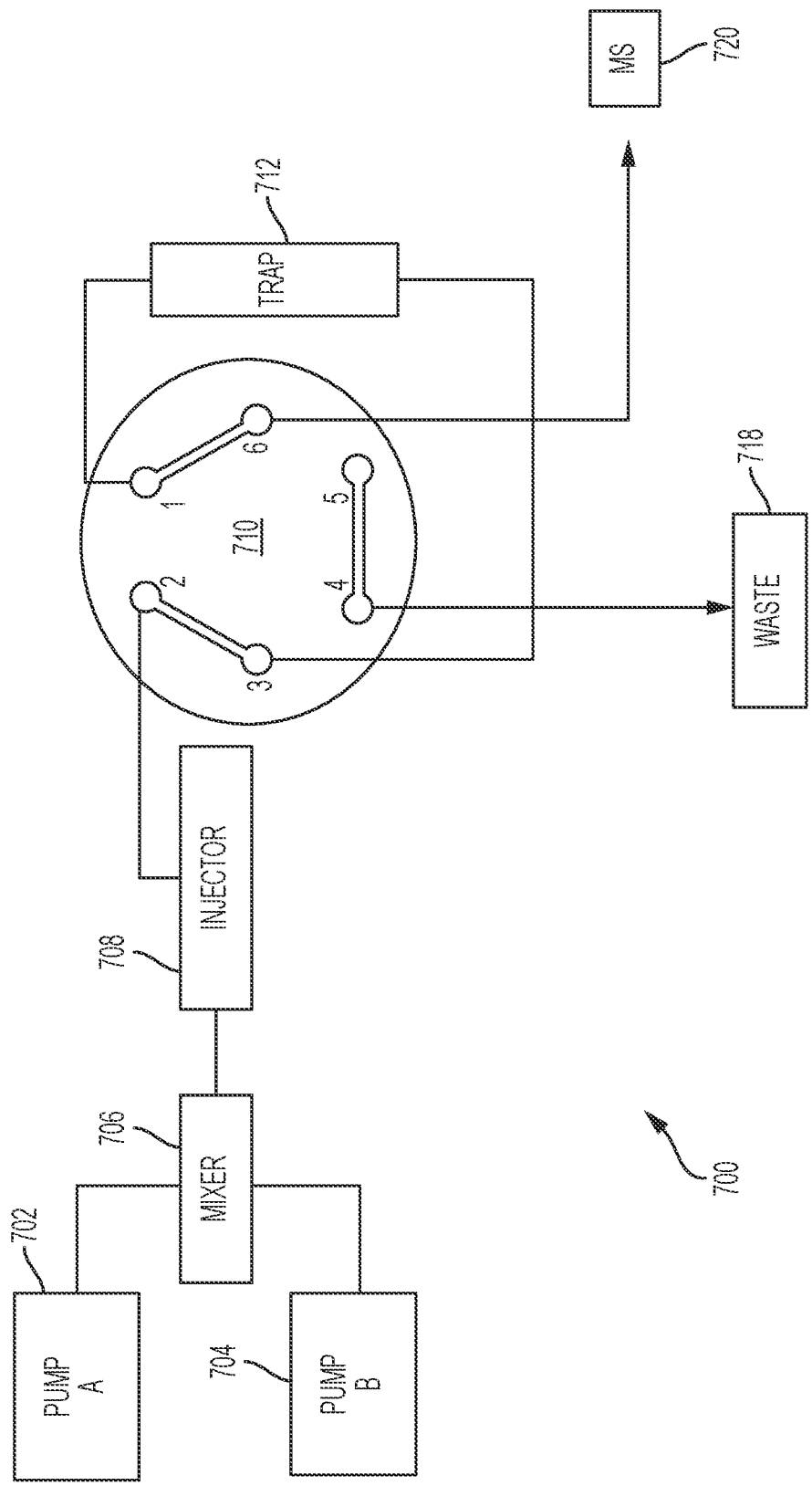
FIG. 7B shows a diagram of trap and elute system according to an embodiment of the invention in a second configuration.

The trap and elute process module 234A may utilize a trap and elute apparatus. The trap and elute process module 234A can involve injecting a sample into a small-volume column where analytes of interest are concentrated before elution into the mass spectrometer. The trapping process optimizes sensitivity and selectivity, and improves robustness. Schematic diagrams of exemplary trap and elute apparatuses are shown in FIGS. 7A and 7B, which are described in further detail below.

In other embodiments, instead of a trap and elute process module, a hydrocarbon (e.g., C18) coated tip can be used. Such tips are commercially available.

The sample introduction process module 230 could also include mechanical reaction vessel transport devices. Such transport devices may include pick and place apparatuses such as pick and place transfer gantrys, transfer shuttles such as extended linear reaction shuttles, or combinations of the pick and place transfer gantrys and extended linear reaction shuttles.

The sample detection process module 240 may include steps that are used to detect the presence, absence, and/or quantity of a particular analyte in a sample. The sample detection process module 240 may include the use of a mass spectrometric process module 240A and/or an optical detection process module 240B. The optical detection process module 240B may use a chemiluminescence or fluorescence based detection process. Other details regarding the mass spectrometric process module 240A and the optical detection process module 240B are provided below.

FIG. 3A shows a high level flowchart 300 illustrating the different types of detection processes that can be performed using the sample processing system according to embodiments of the invention. In the flowchart 300, the ability to detect the presence, absence, and/or concentration of a particular analyte using an optical detection process and a mass spectrometric process is shown. It is apparent that embodiments of the invention have a great deal of flexibility in determining if an analyte is or is not present in a particular sample.

In step 302, an aliquoting station comprising at least one pipettor in the analyzer can obtain two or more or more sample aliquots of a sample and can dispense them into two or more reaction vessels. The at least one pipettor in the aliquoting station may provide (e.g., dispense) a first sample aliquot of the sample to a first reaction vessel. One of the sample aliquots may be subjected to an immunoassay test (an example of a primary analysis) in the immunoanalyzer at step 304. The first reaction vessel including the first sample aliquot may be processed by the immunoanalyzer to form a first processed sample aliquot. Then, the immunoanalyzer may be used to detect if a particular analyte is present or absent in the first processed sample aliquot in the reaction vessel.

After the immunoassay test is performed on the first processed sample aliquot, the control system in the sample processing system can make a decision as to whether a confirmatory test is desired in step 306. If a confirmatory test is desired, the aliquoting station including the at least one pipettor can provide a second sample aliquot of the sample. The second sample aliquot in the second reaction vessel can then be processed by the analyzer to form a second processed sample aliquot. The second processed sample aliquot may be transferred from the analyzer to a mass spectrometer in step 314 via an appropriate sample introduction apparatus. Once the processed second aliquot is in the mass spectrometer, the mass spectrometer may perform a mass analysis (an example of a secondary analysis) on the processed second aliquot in step 310. After the mass analysis is performed on the processed second sample aliquot, a report may be generated in step 312. If a confirmatory test is not desired, then a report may be generated in step 308 without performing a mass spectrometric analysis in step 310.

In some embodiments, data from the immunoanalyzer may indicate that the concentration of the analyte in the first processed sample aliquot is below, above or equal to a predetermined threshold in a primary analysis. The control system may then have determined that a reflex process on the sample may be desirable or necessary. The method may then further include causing the analyzer to process a second aliquot of the sample to form the second processed sample aliquot. The sample introduction apparatus may transfer the second processed sample aliquot from the analyzer to the mass spectrometer. The control system may then cause the mass spectrometer to detect the presence of one or more other analytes in the second processed sample aliquot in a secondary analysis.

In some cases, the detection of the analyte in the primary analysis may indicate that a particular condition (e.g., a medical condition) may be present. However, to confirm that the particular condition is present, the secondary analysis may analyze for a second analyte using mass spectrometry. Together, the presence or absence of the first and second analytes may indicate that the presence of the particular condition is present.

The above described threshold may be any suitable value. For example, the threshold may be that a predetermined quantity (e.g., amount) or concentration of a particular analyte(s) needs to be present in a processed sample aliquot before it can be concluded with a degree of confidence that the analyte is or is not present in the processed sample aliquot.

The use of the mass spectrometric analysis in a reflex process is desirable. In some instances, when a sample is tested for an analyte in a traditional immunoanalyzer, non-specific binding can occur on the antibodies and/or the magnetic beads to which they are attached. This may affect the accuracy of the analysis being conducted. Mass spectrometic analyses are not subject to the problems associated with non-specific binding, and can thus serve as an effective mechanism for reflex testing, or testing in general.

Other methods can also be described with reference to FIG. 3B. In a first exemplary method embodiment, a sample preparation module (e.g., in an analyzer) in a sample processing system can generate a plurality of sample aliquots of a sample at step 322. In step 322, an aliquoting station comprising at least one pipettor or other dispensing device can obtain sample aliquots of one or more samples to one or more reaction vessels. These sample aliquots can be processed to form processed sample aliquots as described herein.

In step 324, a primary analysis comprising a mass spectrometry test can be performed on the processed sample aliquots obtained in step 322. After performing the primary analysis, a report may be generated by the sample processing system in response to the primary analysis in step 322 of the analysis. The presence, absence, or concentration of a particular analyte in the sample can be determined. In some embodiments, the processed sample aliquot may be processed such that one or more analytes within a panel of analytes could be detected if they are present in the sample. The mass spectrometry test 324 may identify one or more analytes in the panel of analytes (e.g., of a number of potential drugs of abuse, a number of proteins that form a panel or a number of steroids that form a panel) in the sample and/or determine the particular amounts of the one or more analytes in the sample. The sample processing system may select the one or more identified analytes in the sample. At this point, the control system of the sample processing system can cause the sample processing system to test the selected one or more samples according to a secondary analysis.

In other embodiments, the secondary analysis may be another confirmatory test on the mass spectrometer in step 326. The sample preparation module can process a sample aliquot of the sample, and transfer the processed sample aliquot back to the mass spectrometer to perform the secondary analysis that includes the second mass spectrometry test 326. The secondary analysis may confirm the presence of the particular one or more analytes in the sample that were identified in the primary analysis. A report may be generated in step 334 after the secondary analysis is completed.

In some embodiments, the secondary analysis may be an immunoassay test (step 328) on the selected one or more samples. The sample preparation module can process a sample aliquot of the sample, and the processed sample aliquot can be processed in the the immunoanalyzer to perform the immunoassay test 328. The immunoassay test can confirm the presence or amount of the one or more analytes identified in the primary analysis. After the secondary analysis, a report may be generated in step 330.

Figure 3B:
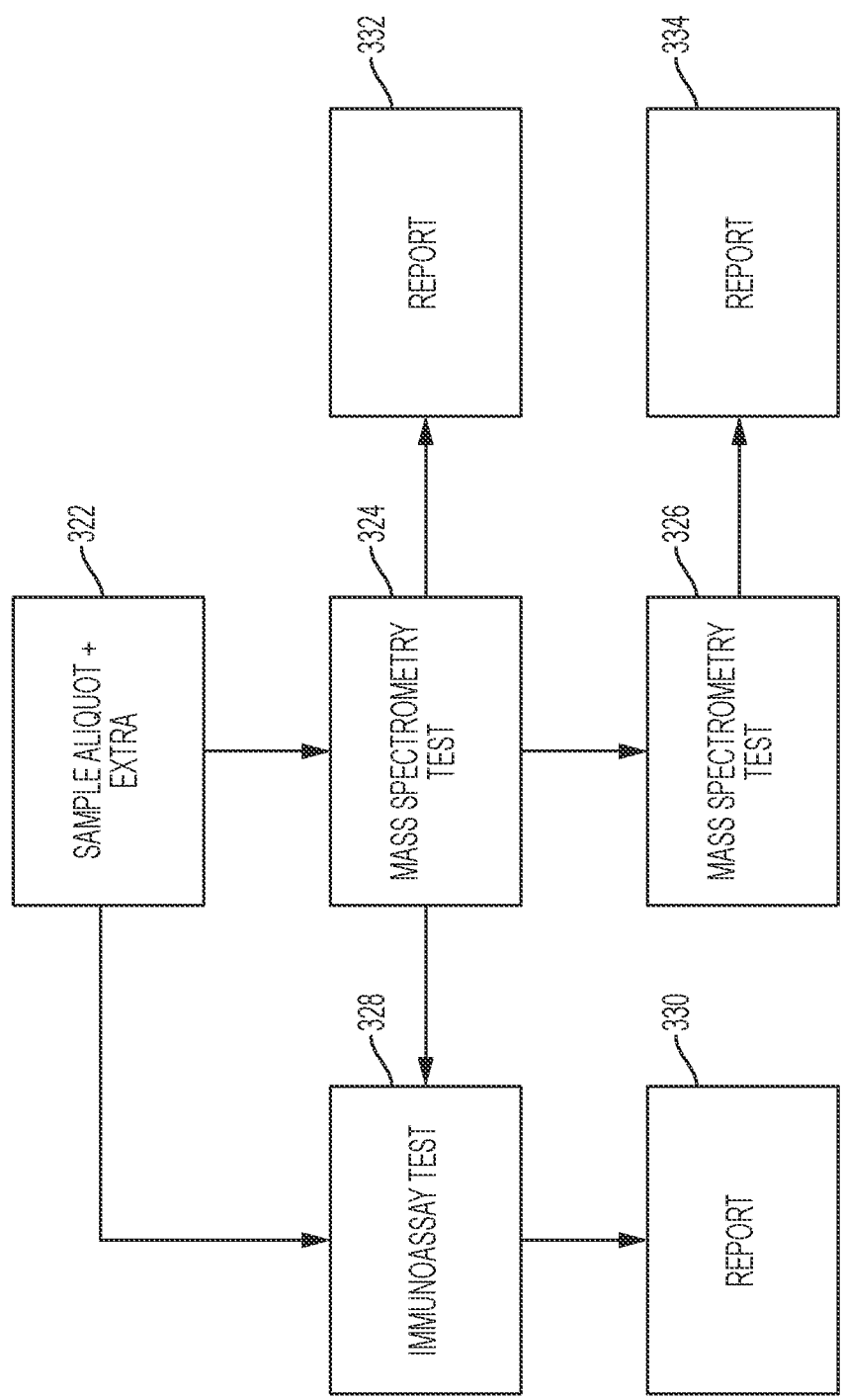

The processes described with respect to FIG. 3B can use a mass spectrometry test to initiatially screen a sample to determine if a particular analyte or set of analytes might be present in a particular sample. Once the initial screening process is completed, then the secondary analysis may be performed to provide confirmation as to the results of the primary analysis. This can be useful if the primary analysis that is performed is a procedure that is not yet an approved by an appropriate authorizing party (e.g., the FDA or Food and Drug Administration). Thus, the method can be used to provide to rapidly perform testing of samples of analytes of interest.

Figure 4A:
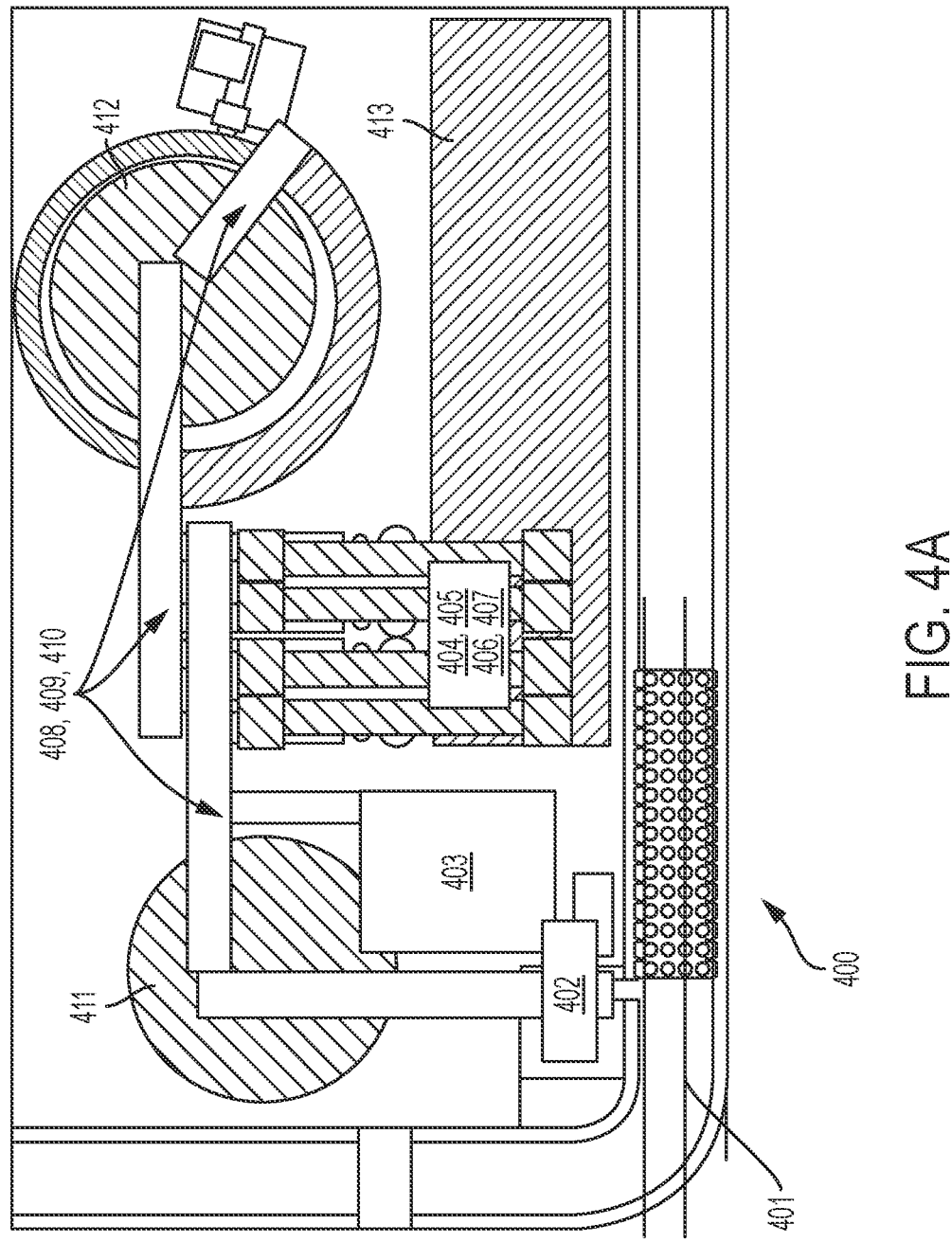
FIG. 4A shows a diagram of an analyzer in a sample processing system according to an embodiment of the invention.

FIG. 4A shows a block diagram of an automated immunochemistry analyzer 400 that can be used in an automated sample processing system according to an embodiment of the invention. The basic structural and functional modules of the automated immunochemistry analyzer 400 can include a sample presentation unit 401, an aliquoting station comprising a main sample pipetting station 402, a bulk vessel feeder 403, first dual reagent pipetting stations 404 and 405, second dual reagent pipetting stations 406 and 407, a first pick-and-place gripper 408, a second pick-and-place gripper 409, a third pick-and-place gripper 410, an incubator/wash/read station 412, a sample storage 411, and a reagent storage 413. Optionally, the sample and/or reagent storage can be chilled.

The sample presentation unit 401 can used to transport an entire required test sample to and from the main sample pipetting station 402. A detailed description of the configurations and functions of the sample presentation unit 401 is provided in U.S. Pat. No. 6,790,413, filed on May 3, 2001, which is incorporated herein by reference in its entirety.

The main sample pipetting station 402 can be used to aspirate samples out of the sample tubes and dispense them into reaction vessels supplied by the bulk vessel feeder 403. A detailed description of the configurations and functions of the bulk vessel feeder 403 is provided in U.S. Pat. No. 6,790,412, filed on Feb. 6, 2001, which is incorporated herein by reference in its entirety.

The four reagent pipetting stations 404, 405, 406, and 407 can be used to mix a sample with reagents for subsequent assays. The four reagent pipetting stations 404, 405, 406, and 407 can be arranged as two dual pipetting stations and can be independent to each other. Each of the four reagent pipetting stations 404, 405, 406, and 407 can have its own fluid pumps and valves, wash towers, reaction vessel carriages, and pipettor(s). Although four pipetting stations 404, 406, 406, 407 are illustrated, it is understood that embodiments of the invention can include more or less of the pipetting stations.

The three vessel pick-and-place grippers 408, 409, 410 can be used to transport sample and reaction vessels among the various modules of the analyzer. The first pick-and-place gripper 408 can be used to transport reaction vessels between the bulk vessel feeder 403 or the sample storage 411 and the reagent pipetting stations 404, 405, 406, 407. The second pick-and-place gripper 409 can be used to transport reaction vessels between the reagent pipetting stations 404, 405, 406, 407 and the incubator of the incubator/wash/read station 412. The third pick-and-place gripper 410 is used to transport reaction vessels between the incubator and the wash wheel (an example of a wash station) of the incubator/wash/read station 412. A detailed description of the configurations and functions of the vessel pick-and-place grippers 408, 409, and 410 is provided in U.S. Pat. No. 7,128,874, which is herein incorporated by reference in its entirety. It is understood that embodiments of the invention can have more or less pick-and-place grippers.

The sample storage 411 can be used for storing the samples contained in the reaction vessels at a low temperature for a certain period of time, e.g., up to three (3) hours, so that the samples may be used for retesting or reflex testing. When a test is requested on a patient sample, the test outcome may drive a request for additional testing. As noted above, this automatic request for additional tests is reflex testing. The time delay from the first aspiration to knowing if another test will be started can range to as long as 45 minutes or more. To hold a sample tube for such a period of time prevents the sample from being used in other places. If the tube is passed to other instruments, it may be difficult for a laboratory technician to find the tube and reload it on the instrument requesting the reflex test. To allow a single quick sample draw on sample tubes that might require reflex testing, a single aspiration (aliquot) can be taken with sufficient test material for the possible reflex test(s). However, to insure that the test materials do not evaporate or deteriorate, the aliquot may need to be refrigerated on board the analyzer.

The sample storage 411 can one or more reaction vessels containing sample aliquots for samples that are being processed in primary analyses. The sample aliquots stored in the sample storage 411 can be used to perform secondary analyses (e.g., reflex tests) on either the analyzer or the mass spectrometer.

Figure 4B:
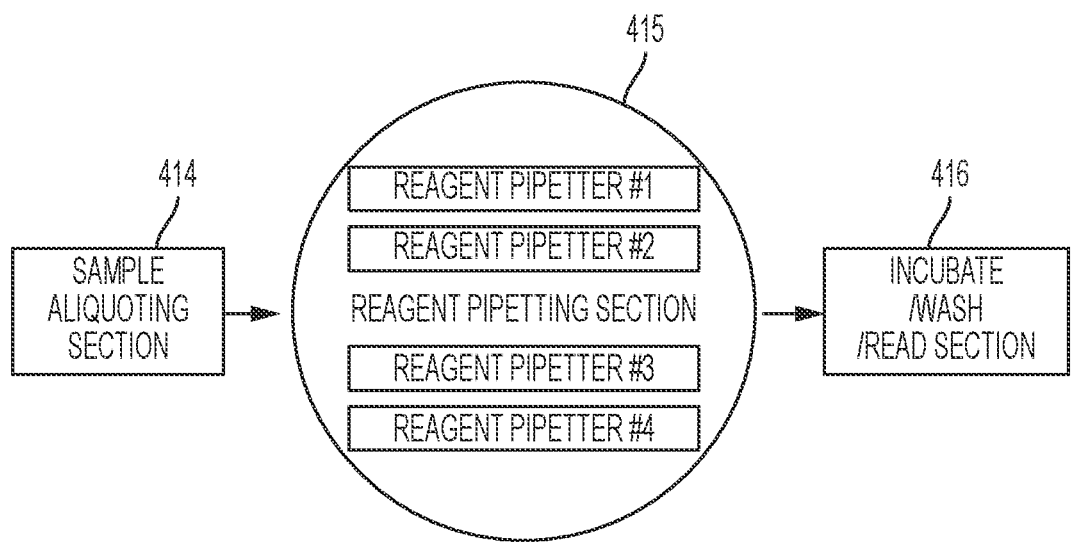
FIG. 4B shows an illustrative flow chart diagram showing operating procedures for operating an analyzer.
Figure 4C:
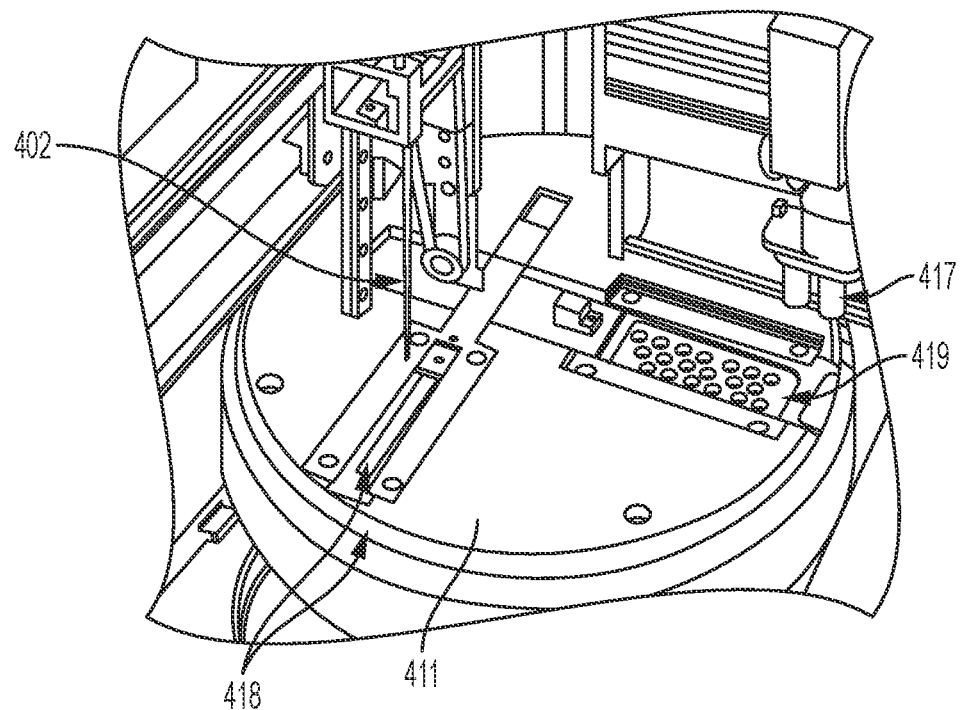
FIG. 4C shows a perspective view showing an arrangement of a main sample pipetting station and a sample storage of the analyzer.

Referring to FIG. 4C, there is shown the arrangement of the main sample pipetting station 402 and the sample storage 411 of the automated immunochemistry analyzer. The pipettor of the main sample pipetting station 402 first aspirates samples from sample tubes, and then moves into a position above the sample storage 411. Meanwhile, the sample storage 411 first receives an empty reaction vessel from the bulk vessel feeder 403 by the pick and place gripper 417, and then moves the empty reaction vessel under the pipettor of the main sample pipetting station 402. The aspirated sample is then dispensed into the chilled reaction vessel. Insulation and doors 418 are provided to control the environment in the sample storage 411. The sample storage 411 can be a precision controlled refrigerator with multiple storage locations 419 capable of receiving and transferring reaction vessels for or filled with sample material. Sample aliquots can be present in reaction vessels that are stored in the sample storage 411. These samples can be used for retesting or reflex testing in the immunoanalyzer or in the mass spectrometer.

The incubator/wash/read station 412 can be used for the incubating, washing, and reading steps of the assays. In some embodiments, the incubator/wash/read station 412 may be generically characterized as a separation station. It may include one or more incubators, one or more assay wash stations, and one or more readers, such as a photomultiplier tube (PMT) detector, or other optical detection systems. A detailed description of the configurations and functions of the incubator/wash/read station is provided in U.S. Pat. No. 7,217,391, filed on Mar. 16, 2001, which is herein incorporated by reference in its entirety.

As a way of minimizing background signals from excess or unbound materials, immunoassays generally use one or more separation phases be carried out in the reaction vessel. To facilitate the separation or washing process, a variety of techniques can be used, including, but not limited to, well coating techniques, bead coating techniques, or the use of paramagnetic particles. Each of these separation media are coated with a capture reagent (e.g., antibody) that will bind analyte molecules of interest in a sample. When paramagnetic particles are used as the separation media, the paramagnetic particles are pulled to the wall of the reaction vessel by magnets during the washing process and the supernatant is aspirated. Luminescent labels are then bound to these analyte molecules. When a luminescing reagent or substrate is added to the reaction vessel, it reacts with the luminescent label to produce light that is detectable by the analyzer's optical detection station.

The reagent storage 413 can be used for storing reagents used for the immunoassays as well as the mass spectrometric process. In some embodiments, the reagent storage may comprise a plurality of reagent packs comprising a first plurality of reagent packs comprising reagents for performing immunoassays, and a second plurality of reagent packs comprising reagents for performing mass analyses in the mass spectrometer.

In some embodiments, reagent packs in the reagent storage 413 may include reagents that are in liquid or solid form. The reagent storage 413 can store reagent packs in a refrigerated environment until requested for use, transfer a pack to an appropriate reagent pipetting station when requested for use, and return the pack to storage when pipetting is complete. It can also return a full or partially used pack to the operator when requested and automatically dispose of empty packs. The temperature in the reagent storage 413 can be controlled by Peltier devices and monitored with a thermistor.

For immunoassays, some types of reagents can include paramagnetic particles with or without coating of antibodies or antigens, blocking agents, antibodies, assay buffers, antibodies conjugated to enzymes (for chemiluminescence), sample pre-treatment reagents such as acids, bases, or releasing agents.

For mass spectrometry, mass spectrometric reagents such as mass tags (e.g., Amplifex™ mass tags) can be used during the sample preparation process to enhance signals and improve sensitivity. As noted above, reagents such as this can be used with the second sample aliquot that will be processed for a mass spectrometric analysis.

The reagent packs can be loaded into the reagent storage 413 as follows: (a) an input tray cover is opened by the operator and the input tray is positioned, if necessary, to allow the operator to place reagent packs into the tray; (b) the input tray cover is closed and the input tray closes, bringing the reagent packs into the reagent storage 413; (c) as the input tray closes, each reagent pack position passes a bar code reader (BCR), where each of the four pack positions is read and identified; (d) a reagent pack gripper of a reagent pack transporting and sorting mechanism moves to get a pack from the input tray that was identified by the bar code reader; (e) the reagent pack gripper of the reagent pack transporting-and-sorting mechanism moves the reagent pack to either a storage location or a pipetting location (if needed), and drops the reagent pack off, and (f) the above steps (d) through (e) can be repeated, until all reagent packs are removed from the input tray.

The reagent storage 413 includes a mechanism for transporting and sorting multiple reagent packs. A detailed description of the configuration and functions of such a mechanism for transporting and sorting multiple reagent packs is provided in U.S. Pat. No. 6,746,648, filed on Jun. 15, 2000. Other structures and functions of the reagent storage 413 conform to existing arrangements known to those of ordinary skill in the art, and therefore will not be described in detail here.

FIG. 4B shows an illustrative flow chart diagram showing the basic operating procedures of the method of automated immunochemistry analysis.

The basic operating procedures of the automated immunochemistry analysis can be carried out in three main sections of the automated immunochemistry analyzer: a sample aliquoting section 414, where the sample is aspirated out of a sample tube and dispensed into a reaction vessel, a reagent pipetting section 415, where the sample is mixed with reagents, and an incubate/wash/read section 416, where the mixed sample is incubated, washed, and separated from particulates and read by the photo-multiplier tube (PMT) detector or other optical detection station.

The sample aliquoting section 414 and the incubate/wash/read section 416 each has one set of units, and works on a cycle (in one embodiment, a nine (9)-second cycle). The reagent pipetting section 415 can have four (4) independently working reagent pipetting stations, where each reagent pipetting station works on second cycle (in one embodiment, a thirty-six (36) second cycle).

However, the scheduling of the four reagent pipetting stations can be staggered (in one example, nine (9) seconds apart). For example, the analyzer can accept one (1) test sample in every nine (9) seconds, i.e., the analyzer has an effective cycle of nine (9) seconds. Accordingly, the analyzer can have a fast throughput (e.g. four hundred (400) tests per hour). Embodiments of the invention are not limited to these timings or values.

Referring to FIGS. 4A and 4B, the basic operating procedures of the sample aliquoting section 414, the reagent pipetting section 415, and the incubate/wash/read section 416 and are described below:

A. The Operating Cycle of the Sample Aliquoting Section 414
1. The user loads a sample rack containing up to four (4) sample tubes on the sample presentation unit 401.
2. The rack is advanced into the main sample pipetting station 402 where the sample may be identified by a bar code reader (BCR) and presented to the main sample pipetting station 402.
3. At the same time, the bulk vessel feeder 403 presents the reaction vessel necessary for the tests to a sample reaction vessel carriage, from where the first pick-and-place gripper 408 picks the reaction vessel up and stores it in the sample storage 411 and/or in the reaction vessel carriage of any one of the available reagent pipetting stations 404, 405, 406, 407.
4. The main sample pipetting station 402 aspirates the amount of sample required and aliquots it into the reaction vessel in the sample storage 411, and afterwards, the probe is washed in its dedicated wash station. The sample probe can be washed to reduce sample carry-over to a level that will not adversely affect other samples.

B. The Operating Cycle of the Reagent Pipetting Section 415
1. The first pick-and-place gripper 408 picks up the reaction vessel containing the aliquotted sample and moves it over to an available reagent pipetting station.

The following describes this process: (a) a requested reaction vessel in the sample storage 411 is positioned under an operating position of the first pick-and-place gripper 408; (b) a reaction vessel carriage of an available reagent pipetting station is positioned under another operating position of the first pick-and-place gripper 408; and (c) the first pick-and-place gripper 408 transfers the requested reaction vessel from the sample storage 411 to the reaction vessel carriage of the available reagent pipetting station.

2. At the same time, the reagent storage 413 brings a required reagent pack to the same reagent pipetting station.
3. With the reagent pack and reaction vessel in position, the reagent pipettor of that reagent pipetting station aspirates a required amount of sample from the sample reaction vessel and dispenses it into an assay reaction vessel and also retrieves a required amount of reagent from the reagent pack and dispenses it into the assay reaction vessel, and afterwards, the probe is washed in its dedicated wash station.

The following describes the process of sample aspiration: (a) the reagent pipettor of the reagent pipetting station is positioned over the reaction vessel; (b) an ultrasonic level sense circuit is used to detect the surface of the sample, and lowering of the pipettor is halted once the surface is found and the pipettor is just deep enough to draw the needed sample volume (therefore reducing carry-over); and (c) the sample is drawn up using the precision pump and valve, where an in-line pressure profile is collected by using a pressure sensor during the sample aspiration, which profile can be used to verify proper sample pickup. A detailed description of the configurations and functions of a precision pump and valve that are used herein are provided in U.S. Pat. Nos. 6,520,755 and 6,843,481, which are herein incorporated by reference in their entirety.

The following describes the process of reagent aspiration: (a) the reagent pipettor of the reagent pipetting station moves to the appropriate reagent well location of the reagent pack; (b) the reagent pipettor is lowered into the reagent pack well, and if this is a particle well, then an ultrasonic mix circuit is enabled (and the lock signal is checked to ensure proper operation) to mix the particles prior to aspiration; and (c) the reagent is drawn up using the precision pump and valve, where an in-line pressure profile is collected by using a pressure sensor during the reagent aspiration, which profile is used to verify proper reagent pickup.

The following describes the process of a sample or reagent delivery: (a) the reagent pipettor of the reagent pipetting station moves to the assay reaction vessel location in the reaction vessel carriage of the pipetting station; (b) the reagent pipettor is lowered into the assay reaction vessel, where the exact dispense height is calculated to have the sample or reagent just touch the probe after it has been dispensed (to ensure that there is no sample or reagent drop left on the tip of the probe); and (c) the sample or reagent is dispensed using the precision piston pump and valve, where an in-line pressure profile is collected by using a pressure sensor during the sample delivery, which profile is used to verify proper sample or reagent delivery.

The following describes the process of sample dilution: (a) the appropriate sample reaction vessel is retrieved for pipetting; (b) the dilution location in a reagent vessel carriage of an available reagent pipetting station is positioned under the operating position of the first pick-and-place gripper 408; (c) the bulk vessel feeder supplies two empty vessels (the reaction vessel and the dilution vessel); (d) the first pick-and-place gripper 408 transfers both vessels simultaneously to the reagent vessel carriage of the available reagent pipetting station; (e) the sample is aspirated and delivered to the dilution vessel along with an additional volume of buffer using the precision piston pump and valve, where the exact dispense height is calculated to have the diluted sample just touch the probe after it has been dispensed (to ensure that there is no sample drop left on the tip of the probe) or to go slightly deeper if mixing is requested (in such case, the ultrasonic mix circuit is enabled and the lock signal is checked to ensure proper operation); (f) a specific volume of this diluted sample is aspirated using the precision pump and valve, where an in-line pressure profile is collected by using a pressure sensor during the aspiration, which profile is used to verify proper diluted sample pickup; (g) the original reaction vessel is returned to the sample storage 411 if there is sample left or is disposed of if it is empty; and (h) the vessel containing the diluted sample now becomes the reaction vessel for the subsequent assay being processed.

The following describes the process of sample and reagent addition: (a) the requested sample is retrieved from the sample storage 411; (b) the bulk vessel feeder supplies an empty reaction vessel to the vessel supply carriage; (c) the vessel supply carriage is positioned under the operating position of the first pick-and-place gripper 408; (d) the reagent vessel carriage of an available reagent pipetting station is positioned under the other operating position of the first pick-and-place gripper 408; (e) the first pick-and-place gripper 408 transfers the empty reaction vessel to the reagent vessel carriage of the available reagent pipetting station; (f) the reagent vessel carriage is positioned for pipetting; (g) the requested reagent pack is also positioned for pipetting; (h) the reagent pipettor of the reagent pipetting station moves to a reagent wash tower, then down into the reagent wash tower, for washing the probe; (i) the sample is aspirated and delivered to the reaction vessel; (j) the reagent pipettor moves to the reagent wash tower, then down into the reagent wash tower, for washing the probe; (k) the reagent pipettor aspirates the appropriate amount of reagent and delivers it to the reaction vessel; (l) the above steps (j) and (k) are repeated until all of the reagents have been delivered to the reaction vessel; (m) if reaction vessel mixing is desired, the probe moves down slightly and the ultrasonic mix circuit is enabled and the lock signal is checked to ensure the proper operation; (n) the reagent vessel carriage is positioned under an operating position of the second pick-and-place gripper 409; (o) an empty position on a reaction vessel incubator wheel is positioned under another operating position of the second pick-and-place gripper 409; (p) the second pick-and-place gripper 409 transfers the reaction vessel into the incubator of the incubating/wash/read station 412; (q) in the case of two or three step assays, the second pick-and-place gripper 409 will bring the reaction vessel back to a pipetting location and additional reagents will be added, and then the vessel is transferred back to the incubator of the incubating/wash/read station 412 by the second pick-and-place gripper 409 for the second or third incubation.

The reagent probe can be washed to reduce sample and reagent carry-over to a level that will not adversely affect other samples or reagent. The following describes this process: (a) the ultrasonic circuit is enabled to wash the reagent probe; (b) a vacuum pump evacuates the tower, while the tower's evacuation line pressure is monitored to ensure that the tower is draining properly; (c) the probe is flushed internally with buffer using the precision pump and precision valve and showered externally using the peristaltic pump; and (d) the buffer flow is stopped while the vacuum pump and ultrasonic circuit run slightly longer to ensure that the probe is dried.

4. The second pick-and-place gripper 409 picks up the assay reaction vessel containing the mixture of sample and reagent and moves it over to an incubator wheel of the incubator/wash/read station 412.
5. The first pick-and-place gripper 408 picks up the sample reaction vessel containing the remaining aliquotted sample and returns it to the sample storage 411 if reflex testing is required or else ejects it to a waste container.

The following describes this process: (a) a sample storage location in the sample storage 411 is positioned under the operating position of the first pick-and-place gripper 408; (b) the reaction vessel carriage of the reagent pipetting station is positioned under the other operating position of the first pick-and-place gripper 408; and (c) the first pick-and-place gripper 408 transfers the sample reaction vessel from the reaction vessel carriage of the available reagent pipetting station to the sample storage 411.

C. The Operating Cycle of the Incubate/Wash/Read Section 416

1. The assay vessel remains in the incubator wheel for a programmed time at a controlled temperature with heater elements and is monitored with a thermistor, and then picked up by the third pick-and-place gripper 410 for washing.
2. The wash/read ring has multiple aspirate stations and multiple dispense stations and the assay reaction vessel goes through several operations, including particle washing, substrate addition and incubation, etc., under a controlled temperature with heater elements and monitored with a thermistor.
3. The assay reaction vessel is read by the reader/detector, and thereafter is put back to the incubator by the third pick-and-place gripper 410, and thereafter picked up and disposed in the waste container by the second pick-and-place gripper 409.

The operations of the analyzer are supported by fluid systems, electronic control hardware; and software, including various sensors and micro-controller(s), electrical power supply units, motors, and driving mechanisms, and mechanical structures, and the determination of suitable materials and structures are within the skill in the art.

The method performed in an automated immunochemistry analysis can also include the following steps: (a) adjusting the respective cycle of at least one of the at least two procedures, such that one of the least two procedures has an operating cycle of a first period of time and another one of the at least two procedures has an operating cycle of a second period of time, and the quotient of the second period of time divided by the first period of time is a whole number; (b) providing a plurality of independent working stations for performing the other one of the at least two procedures, each working station operating on the cycle of the second period of time, such that the number of such stations equal to the whole number; and (c) staggering apart respective cycles of the independent working stations by the first period of time, such that at least one of the working stations is available for each operating cycle of the first period of time.

The analyzer has many unique features and advantages. First, the analyzer can be capable of having a high throughput, e.g., 400 tests per hour. Second, the analyzer can be capable of providing multiple pipetting modules that can work independently to ensure uninterrupted analysis, even when one of the modules malfunctions. Third, the analyzer can perform retesting or reflex testing with a large capacity sample storage area.

Figure 5A:
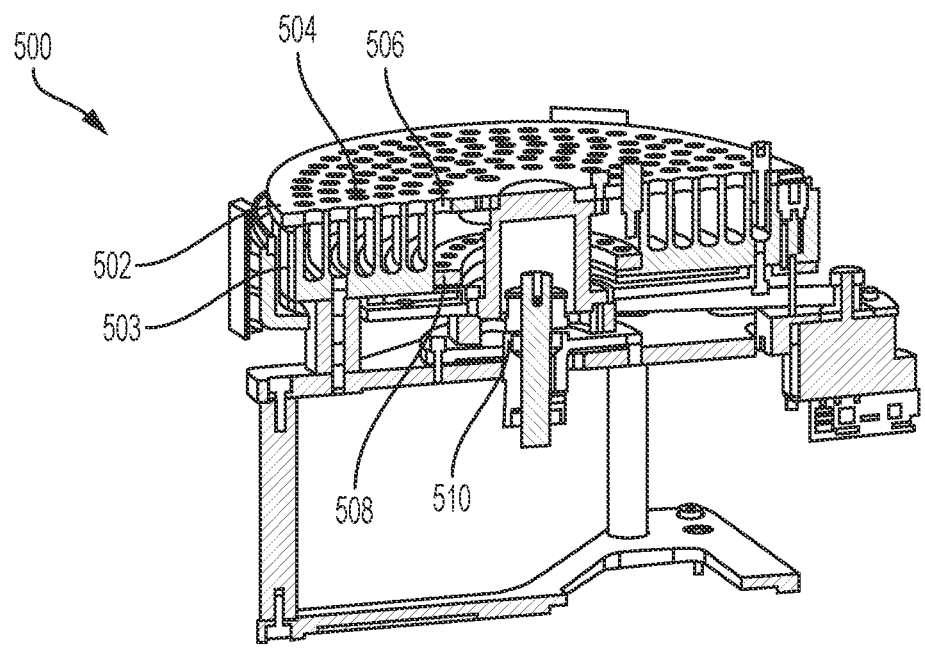
FIG. 5A shows a top/side cross-sectional view of an incubation carousel according to an embodiment of the invention.
Figure 5B:
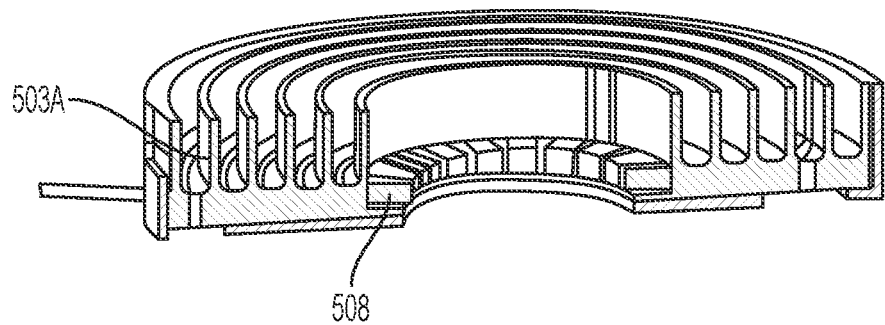
FIG. 5B shows a top/side perspective and cross-sectional view of a portion of the incubation carousel in FIG. 5A.
Figure 5C:
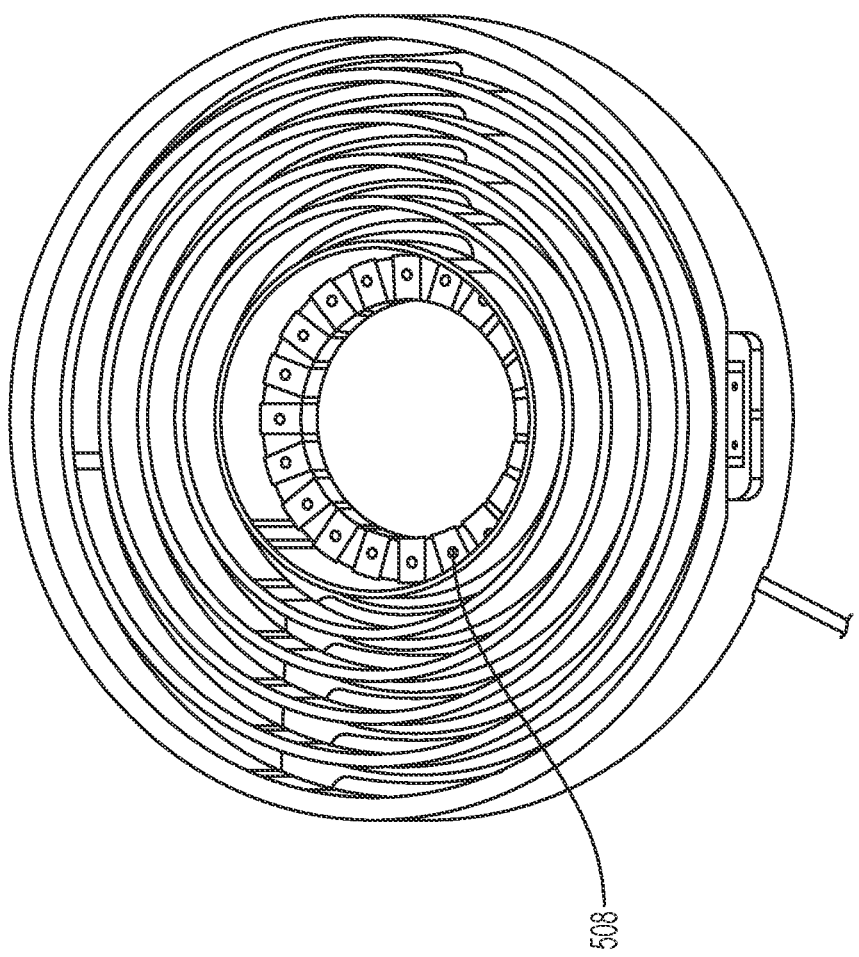
FIG. 5C shows a top perspective view of a portion of the incubation carousel in FIG. 5A.

FIG. 5A shows a cross-sectional view of an incubation carousel 500 according to an embodiment of the invention. FIG. 5B shows a cross-section of a portion of the incubation carousel 500. FIG. 5C shows a top perspective view of a portion of the incubation carousel 500.

Referring to FIG. 5A, the incubation carousel 500 can include a body including a top portion 502 in the form of a circular plate with an array of holes 504 for receiving reaction vessels with samples to be processed. Each hole 504 may correspond to a discrete incubation region where a reaction vessel may be subjected to an incubation process. The top portion 502 sits on top of a bottom portion 503, which includes a number of concentric walls 503A (shown in FIG. 5B). The body is situated on an axis 510 that can cause the incubation carousel 500 to rotate. If desired, heaters such as thin film heating elements may be included within the body so that samples within the holes 504 can be heated if desired. The incubator carousel 500 can have other shapes, or more or less holes than are specifically illustrated.

Magnets 508 can be present within the bottom portion 503 of the body of the incubation carousel. 500. As shown in FIGS. 5A-5C, the magnets 508 are present in the innermost circle of incubation regions, but they part of any suitable number of incubation regions. The magnets may used to bind magnetic particles so that any supernatant that is suitable for a downstream mass spectrometric analysis can be performed. The magnets may be permanent magnets or electromagnets. An aspiration device (not shown) such as a pipettor may remove any supernatant and may transfer the supernatant to a sample introduction apparatus, for eventual transfer to the mass spectrometer.

A wide variety of mass analyzer systems, which can form part of the mass spectrometers, can be used in the sample processing system according to embodiments of the invention. Suitable mass analyzer systems include two mass separators with an ion fragmentor disposed in the ion flight path between the two mass separators. Examples of suitable mass separators include, but are not limited to, quadrupoles, RF multipoles, ion traps, time-of-flight (TOF), and TOF in conjunction with a timed ion selector. Suitable ion fragmentors include, but are not limited to, those operating on the principles of: collision induced dissociation (CID, also referred to as collisionally assisted dissociation (CAD)), photoinduced dissociation (PID), surface induced dissociation (SID), post source decay, by interaction with an electron beam (e.g., electron induced dissociation (EID), electron capture dissociation (ECD)), interaction with thermal radiation (e.g., thermal/black body infrared radiative dissociation (BIRD)), post source decay, or combinations thereof.

Examples of suitable mass spectrometers include, but are not limited to, those which comprise one or more of a triple quadrupole, a quadrupole-linear ion trap (e.g., 4000 Q TRAP® LC/MS/MS System, Q TRAP® LC/MS/MS System), a quadrupole TOF (e.g., QSTAR® LC/MS/MS System), and a TOF-TOF.

In various embodiments, the mass spectrometer comprises a MALDI ion source. In various embodiments, at least a portion of the combined sample is mixed with a MALDI matrix material and subjected to parent-daughter ion transition monitoring using a mass analyzer with a MALDI ionization source.

The mass spectrometer can comprise a triple quadrupole mass spectrometer for selecting a parent ion and detecting fragment daughter ions thereof. In this embodiment, the first quadrupole selects the parent ion. The second quadrupole is maintained at a sufficiently high pressure and voltage so that multiple low energy collisions occur causing some of the parent ions to fragment. The third quadrupole is selected to transmit the selected daughter ion to a detector. In various embodiments, a triple quadrupole mass spectrometer can include an ion trap disposed between the ion source and the triple quadrupoles. The ion trap can be set to collect ions (e.g., all ions, ions with specific m/z ranges, etc.) and after a fill time, transmit the selected ions to the first quadrupole by pulsing an end electrode to permit the selected ions to exit the ion trap. Desired fill times can be determined, e.g., based on the number of ions, charge density within the ion trap, the time between elution of different signature peptides, duty cycle, decay rates of excited state species or multiply charged ions, or combinations thereof.

One or more of the quadrupoles in a triple quadrupole mass spectrometer can be configurable as a linear ion trap (e.g., by the addition of end electrodes to provide a substantially elongate cylindrical trapping volume within the quadrupole). In various embodiments, the first quadrupole selects the parent ion. The second quadrupole is maintained at a sufficiently high collision gas pressure and voltage so that multiple low energy collisions occur causing some of the parent ions to fragment. The third quadrupole is selected to trap fragment ions and, after a fill time, transmit the selected daughter ion to a detector by pulsing an end electrode to permit the selected daughter ion to exit the ion trap. Desired fill times can be determined, e.g., based on the number of fragment ions, charge density within the ion trap, the time between elution of different signature peptides, duty cycle, decay rates of excited state species or multiply charged ions, or combinations thereof.

In some embodiments, the mass spectrometer can comprise two quadrupole mass separators and a TOF mass spectrometer for selecting a parent ion and detecting fragment daughter ions thereof. In various embodiments, the first quadrupole selects the parent ion. The second quadrupole is maintained at a sufficiently high pressure and voltage so that multiple low energy collisions occur causing some of the ions to fragment, and the TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof.

In some embodiments, the mass spectrometer can comprise two TOF mass analyzers and an ion fragmentor (such as, for example, CID or SID). In various embodiments, the first TOF selects the parent ion (e.g., by deflecting ions that appear outside the time window of the selected parent ions away from the fragmentor) for introduction in the ion fragmentor and the second TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof. The TOF analyzers can be linear or reflecting analyzers.

The mass spectrometer can comprise a tandem MS-MS instrument comprising a first field-free drift region having a timed ion selector to select a parent ion of interest, a fragmentation chamber (or ion fragmentor) to produce daughter ions, and a mass separator to transmit selected daughter ions for detection. In various embodiments, the timed ion selector comprises a pulsed ion deflector. In various embodiments, the ion deflector can be used as a pulsed ion deflector. The mass separator can include an ion reflector. In various embodiments, the fragmentation chamber is a collision cell designed to cause fragmentation of ions and to delay extraction. In various embodiments, the fragmentation chamber can also serve as a delayed extraction ion source for the analysis of the fragment ions by time-of-flight mass spectrometry.

In some embodiments, ionization can be used to produce structurally specific fragment ions and Q3 MRM ions. A labeling reagent can be wholly or partly contained in the structurally specific fragment ions. The method can provide both sensitivity and specificity for the Q3 MRM ions. In some embodiments, ionization can be used to produce a dominant neutral loss fragment ion which can be selected in Q3 and then fragmented to produce structurally specific ions. These fragment ions can then be used for identification and quantification in a procedure referred to as MS3.

Figure 6A:
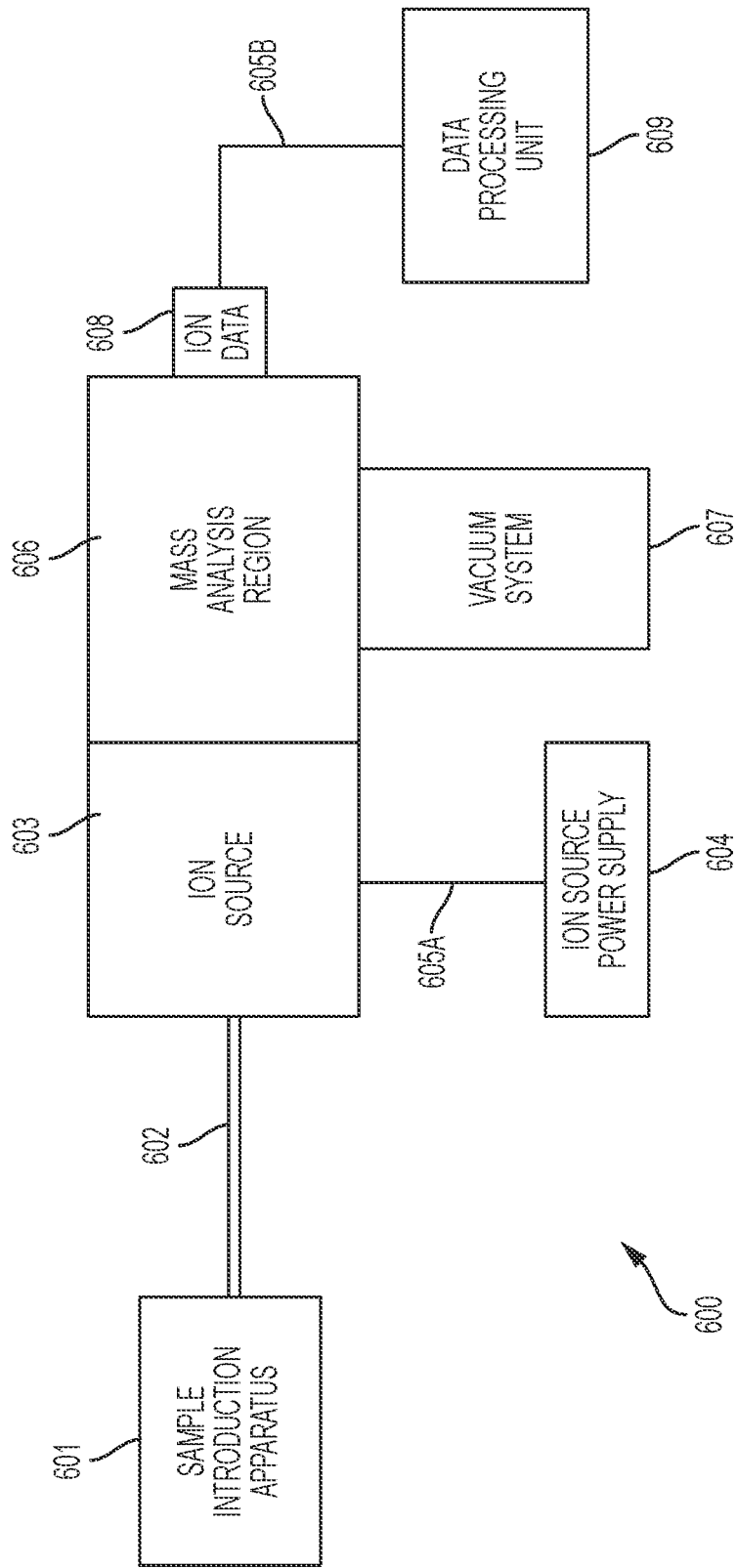
FIG. 6A shows a block diagram of a mass spectrometer.

FIG. 6A shows a block diagram of an exemplary mass spectrometer 600 and a sample introduction apparatus 601 coupled to the mass spectrometer. A sample solution may have been transferred from the analyzer, into the sample introduction apparatus 601. The sample introduction apparatus 601 can be in the analyzer in some embodiments. The sample introduction apparatus 601 may be coupled to the mass spectrometer 600 through a connecting tube 602. The sample introduction apparatus 601 may introduce the sample solution to the ion source 603 through the connecting tube 602. The ion source 603 can be controlled by an ion source power supply 604 through a signal line 605A. Ions concerning sample molecules, which are generated by the ion source 603, are introduced to a mass analysis region 606 and mass analyzed. The mass analysis region 606 is evacuated to a vacuum by a vacuum system 607. The ions thus mass analyzed are detected by an ion detector 608. A detection signal is fed through a signal line 605B to a data processing unit 609. The data processing unit 609 may be a separate unit or may be part of the previously described control system.

Figure 6B:
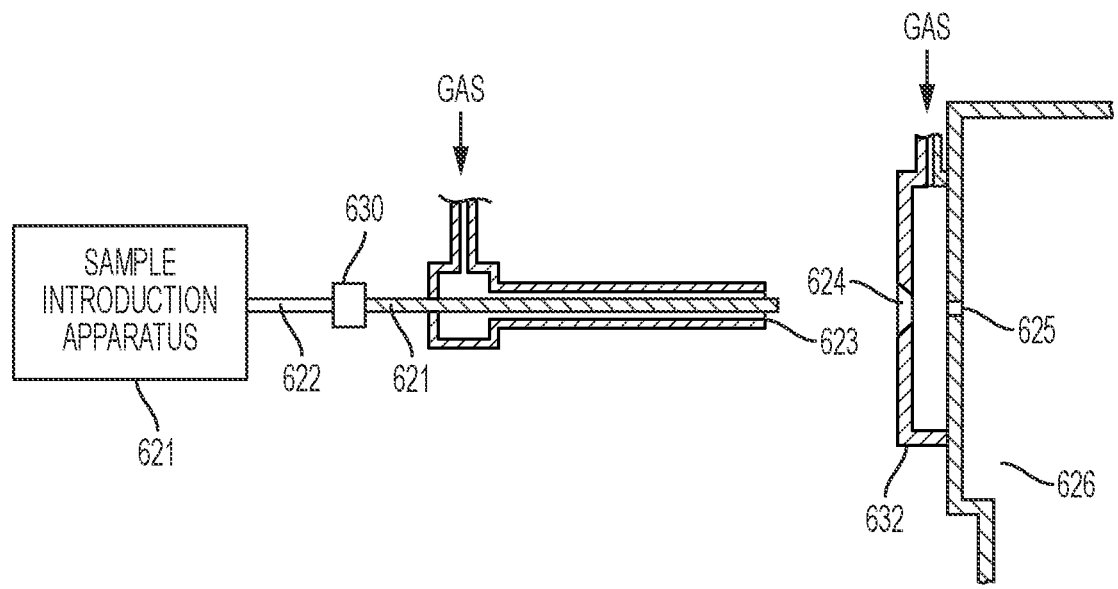
FIG. 6B shows a portion of a mass spectrometer using an electrospray method.

FIG. 6B shows a diagram of a portion of a mass spectrometer using an electrospray method. FIG. 6B is a sectional view showing the structure of a sample introduction apparatus 619 coupled to an electrospray ion source. A sample solution provided from the sample introduction apparatus 619 is introduced through a connecting tube 622 and a connector 630 into a capillary 621 for nebulization. By application of a voltage of the order of kV between the nebulization capillary 621 and a counter electrode 632, small charged droplets of the sample solution are conically nebulized from an end of the nebulization capillary, that is, a so-called electrospray phenomenon occurs. In the electrospray method, an output 623 for nebulizing gas is provided so that gas such as nitrogen gas is poured from the surroundings of the nebulization capillary 621 to thereby accelerate the vaporization of the small charged droplets. Further, the gas such as nitrogen gas is blown toward the generated small charged droplets from an outlet 624 for vaporizing gas provided in the counter electrode 632 side to thereby accelerate the vaporization of the small charged droplets. Ions thus generated are introduced through an ion sampling aperture 625 into a vacuum 626 and mass analyzed by a mass analysis region 626 under a high vacuum.

Figure 6C:
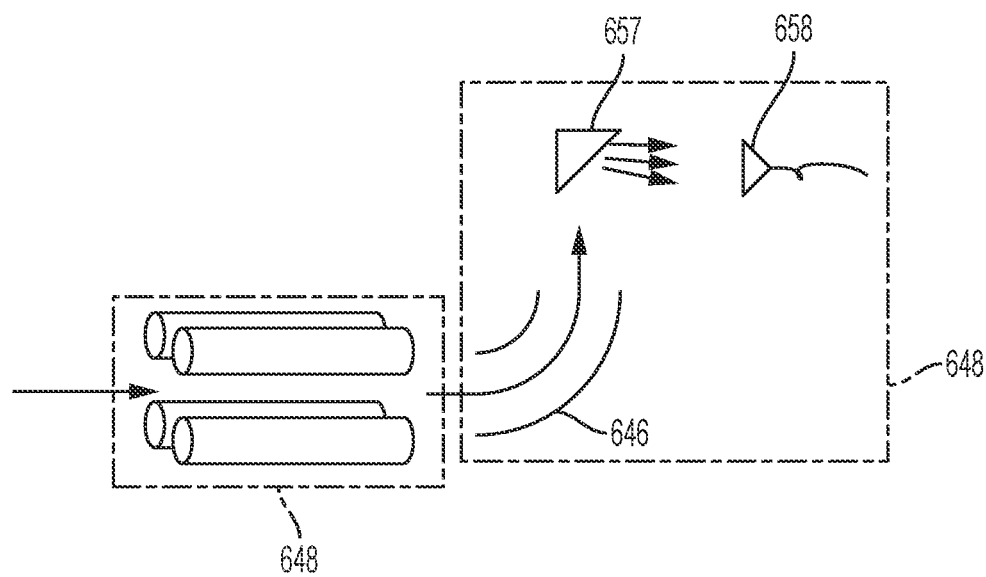
FIG. 6C shows a structure of an ion detector used in a mass spectrometer.

FIG. 6C shows a structure of an ion detector. The structure shown in FIG. 6C can be used to improve the signal-to-noise ratio (SIN) in the mass spectrometer. An ion deflecting electrode 646 can be provided in the rear portion of a mass analysis region 648 for mass separation under a high-frequency electric field to deflect mass-separated ions. The deflected ions are accelerated at a voltage of the order of kV and collide with a dynode 657 to produce secondary electrons. Secondary electrons are emitted from the secondary electron-producing dynode 657 with which the ions collide. The emitted secondary electrons are detected by an electron detector 658 such as an electron multiplier. By the structure shown in FIG. 6C, neutral molecules having no charge, charged droplets or droplets having no charge are prevented from being detected as a signal by the ion detector 648, so that improvement in S/N is attained.

As noted above, a sample introduction apparatus may be disposed between the analyzer and the mass spectrometer. One type of sample introduction apparatus can be a trap and elute apparatus. Details of a suitable trap and elute apparatus can be described with reference to FIGS. 7A and 7B.

FIG. 7A shows a diagram of components in a trap and elute apparatus 700 according to an embodiment of the invention in a first configuration. FIG. 7B shows the trap and elute system 700 according to an embodiment of the invention in a second configuration.

The trap and elute apparatus 700 includes a first pump 702 and a second pump 704, which are in fluid communication with a mixer 706. An injector 708 is downstream of and in fluid communication with the mixer 706. The injector 708 can interface with a series of valves 710. Connection points in the series of valves may be labeled 1-6. The series of valves may be present in a switching valve device 710, which may connect to a trap 712, and may connect or disconnect the trap 712 from a downstream waste station 718 or a downstream mass spectrometer 720. The trap 712 may contain any suitable material such as a C18 material.

In FIG. 7A, a sample to be processed in the mass spectrometer 720 may be pumped by pump A 702 into the mixer 706, and into the injector 708. It may then be injected into the series of valves in the switching valve device 710 (the connection points 1-2, 3-4, and 5-6 may be connected) and may flow through the trap and to the waste station. Any analyte of interest may be captured in the trap 712, and any liquid component of the sample that is not of interest may be transferred to the waste station 718.

In FIG. 7B, the connection points in the series of valves in the switching valve device 710 are switched. Now, connection points 2-3, 1-6, and 4-5 are connected. As shown, a buffer that is compatible with the mass spectrometer 720 may be pumped from the second pump 704, to the mixer 706, and to the injector 708. The injector 708 may then inject the buffer to the trap 712 and the buffer will elute any analyte of interest off of the trap 712 and into the mass spectrometer 720.

The sample processing system may be capable of performing any suitable analysis on any suitable analyte in any suitable sample. Such analyses may include immunopurification and detection processes, protein precipitation and detection processes, and SISCAPA-type processing methods. Rather than measure an intact protein directly by mass spectrometry, SISCAPA makes use of proteolytic digestion (e.g., with the enzyme trypsin) to cleave sample proteins into smaller peptides ideally suited to quantitation by mass spectrometry. By selecting a target peptide whose sequence occurs only in the selected target protein (a so-called "proteotypic" peptide), the target peptide can serve as a direct quantitative surrogate for the target protein. A synthetic version of the target peptide containing a stable isotope label can added in a known amount to the digested sample to serve as an internal standard (SIS). Since the target peptide and SIS are chemically indistinguishable throughout the workflow, but can be measured separately by a mass spectrometer due to the mass difference of the stable isotope label, their ratio provides the desired quantitative estimate of the target peptide amount.

Figure 8:
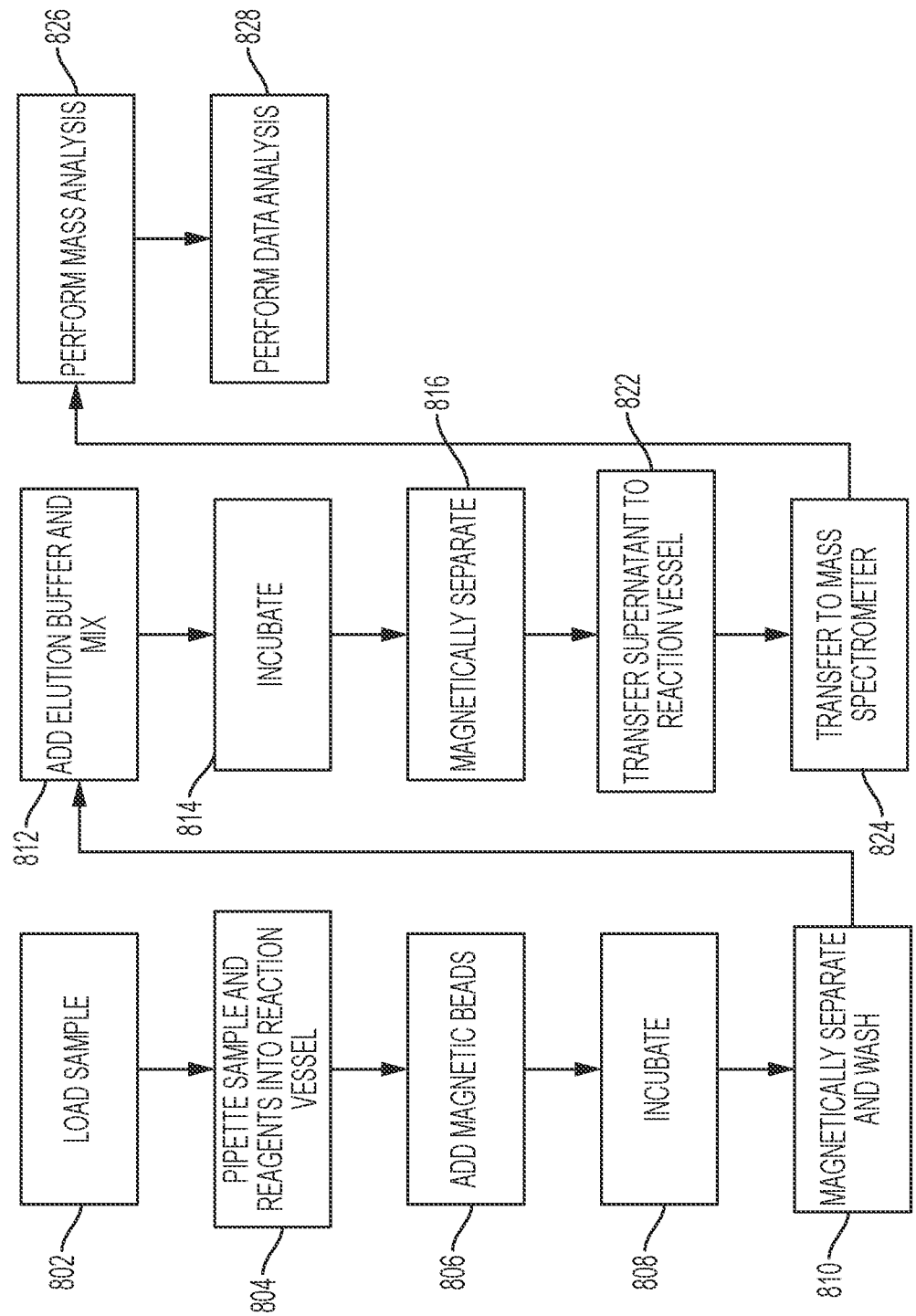
FIG. 8 shows a flowchart illustrating an immunopurification process according to an embodiment of the invention.
Figure 9:
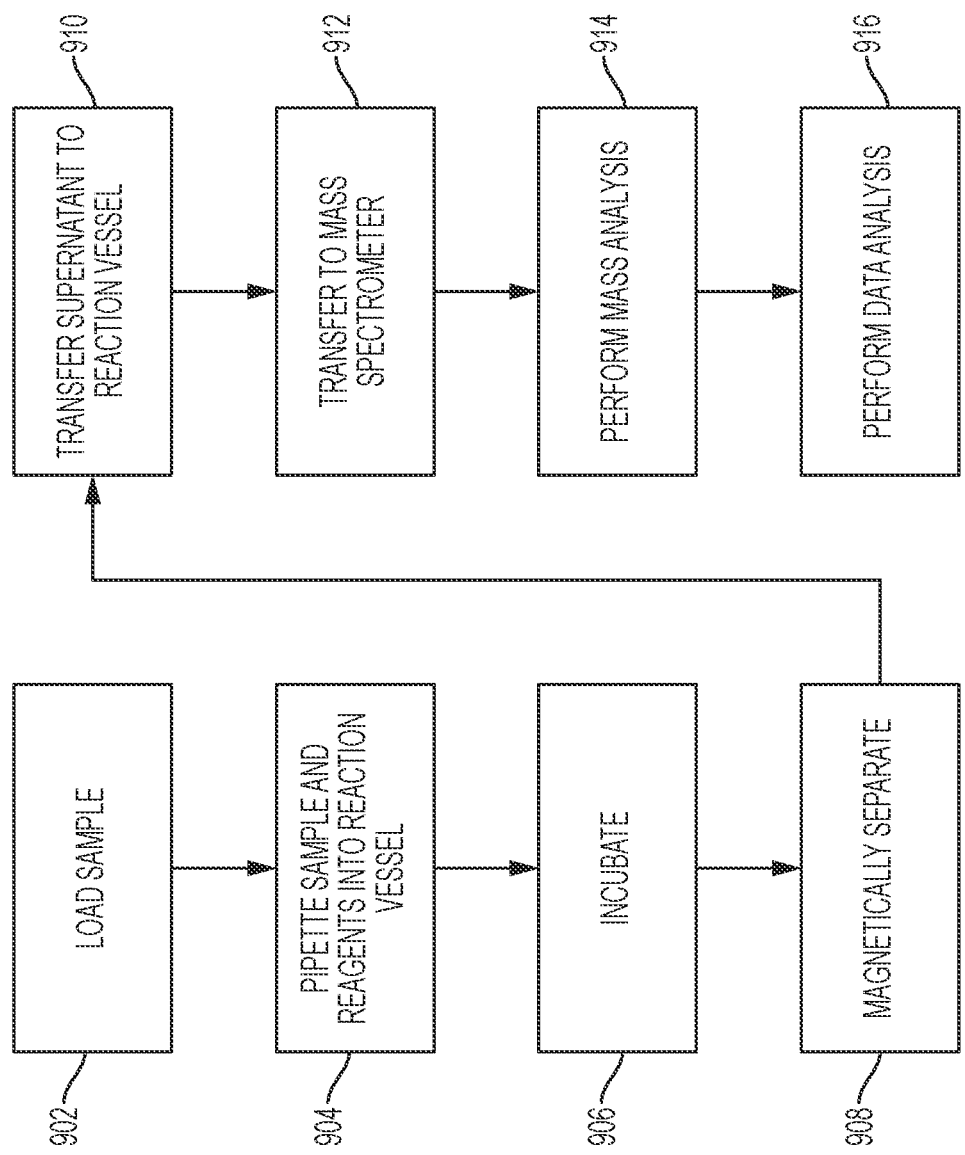
FIG. 9 shows a flowchart illustrating a protein precipitation process according to an embodiment of the invention.
Figure 10:
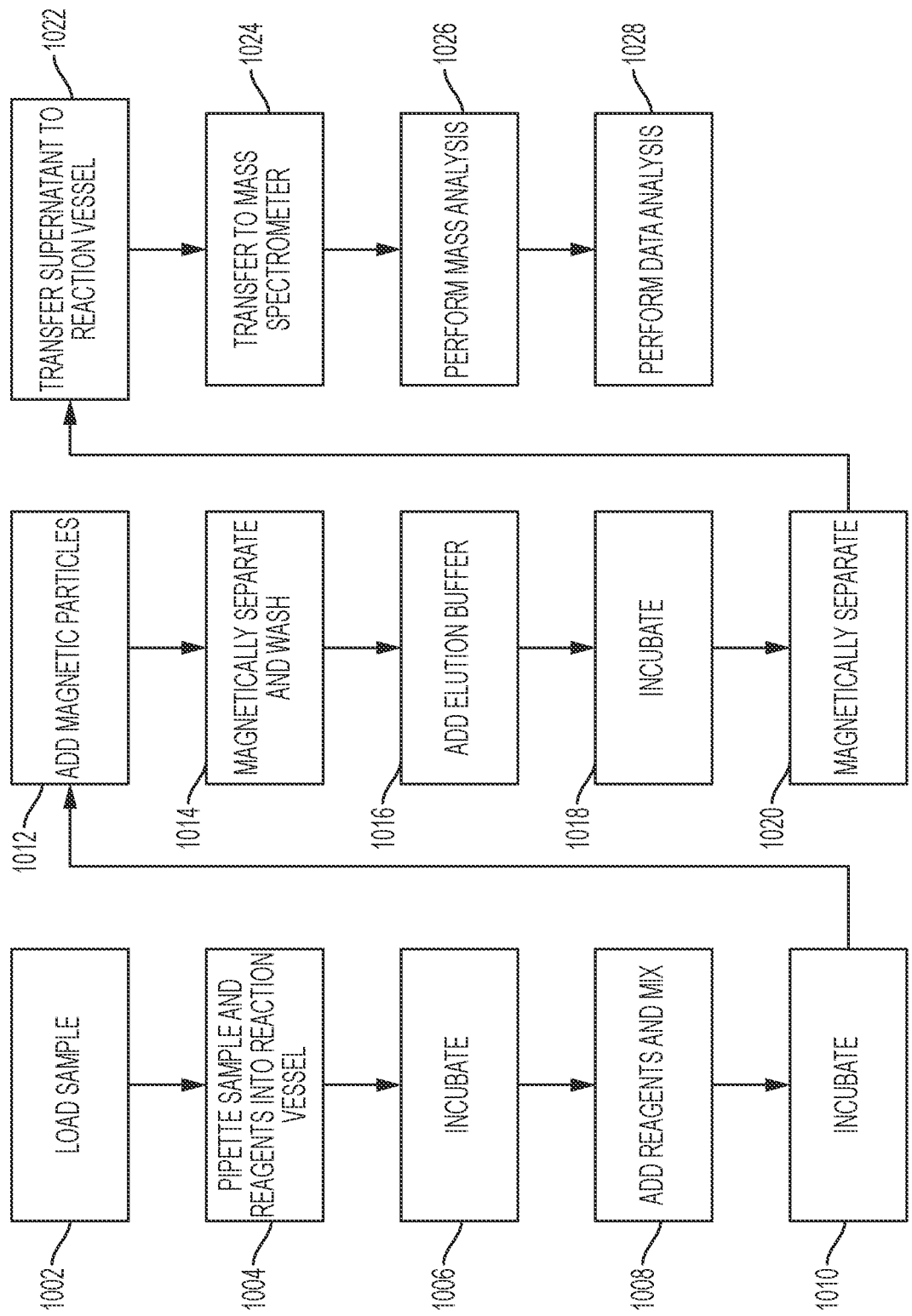
FIG. 10 shows a flowchart illustrating another immunopurification process according to an embodiment of the invention.

FIGS. 8-10 illustrate processes that utilize the analyzer to prepare a sample for a mass spectrometric analysis, and the subsequent mass analysis performed by the mass spectrometer.

FIG. 8 shows a flowchart illustrating an immunopurification process according to an embodiment of the invention. Reference can be made with respect to the analyzer diagram in FIG. 4A above.

In step 802, a sample in a sample tube is loaded into the sample presentation unit 401 in the analyzer 400. The sample tube may be present along with a number of other sample tubes in a sample tube rack or other sample tube carrier.

In step 804, the main sample pipetting station 402 may then pipette one or more aliquots of the sample in the sample tube into one or more reaction vessels provided by the bulk vessel feeder 403. At this point, the first pick and place gripper 408 may transfer the reaction vessel to the reagent pipetting stations 404, 405, 406, 407. If two sample aliquots are present in two reaction vessels, then one of the reaction vessels may be transported by the first pick and place gripper 40 to the sample storage 412 for possible future reflex testing or retesting by either the immunoanalyzer or the mass spectrometer. In some cases, a single reaction vessel with a sample aliquot may be stored in the sample storage 412 and may be used for multiple tests (e.g. by taking a secondary aliquot from the reaction vessel and transferring to a third vessel). In some cases, 5-10 tests can be run from the initial aliquot in a reaction vessel.

In step 806, in one of the reagent pipetting stations 404, 405, 406, 407, magnetic beads coated with an analyte specific capture antibody may be added to the sample aliquot in the reaction vessel along with any other suitable reagents. The reagent and the sample aliquot may then be mixed in the reagent pipetting station. Mixing can take place by using a pipettor to aspirate and dispense fluid inside of a reaction vessel repeatedly or by any other suitable mixing process. Note also that even though reagents are described as being pipetted in this and other examples, it is understood that reagents may be added to reaction vessels in any suitable manner. For example, dry reagents may be present or added to reaction vessels before or after sample aliquots are added to them.

After the appropriate reagents are added to the reaction vessel containing the sample aliquot, the second pick and place gripper 409 may transfer the reaction vessel to the incubator/wash/read station 412.

In step 808, in the incubator in the incubator/wash/read station 412, the reaction vessel containing the magnetic beads and the sample may be incubated to capture any analyte of interest on the antibodies attached to magnetic particles. The mixture in the reaction vessel may be incubated for any suitable amount of time (e.g., 60 minutes).

In step 810, in the wash apparatus in the incubator/wash/read station 412, the magnetic beads may be washed with a wash fluid, and magnetically separated from the supernatant. A pipettor in the wash apparatus can be used to dispense and remove any fluid from the reaction vessel to perform this process.

Once the washing process is completed, the second pick and place gripper 409 may then transport the reaction vessel to the reagent pipetting stations 404, 405, 406, 407. Once the analyte of interest is bound to the antibodies on the magnetic particles, the control system can determine if an immunoassay detection process or a mass spectrometric analysis process is to be performed. In some cases, the determination as to whether an immunoassay detection process or a mass spectrometric analysis process is to be performed can be made earlier in the process.

If an immunoassay detection process is to be performed, then one of the pipetting stations 404, 406, 406, 407 may dispense a chemiluminescent substrate or other optical substrate into the reaction vessel. Alternatively, the substrate can be added to the reaction vessel by a dedicated pipettor in the washing system. The reaction vessel may then be transferred by the second pick and place gripper 409 to the incubator in the incubator/wash/read station 412. In the incubator, the chemiluminescent substrate may bind to the analyte of interest, still bound to the magnetic beads. The reaction vessel may then be transferred from the incubator to the reader in the incubator/wash/read station 412 using the third pick and place gripper 410. The reader may then detect if analyte is present and/or the concentration of the analyte.

In some embodiments of the invention, the detection process may be performed by a mass spectrometer. Steps 812, 814, 816, 822, 824, 826, and 828 can be performed when a mass spectrometer is used to detect the presence or concentration of the analyte in the sample.

In step 812, instead of adding one or more optical detection reagents (e.g., a chemiluminescent subtract) into the reaction vessel, one of the reagent pipetting stations 404, 405, 406, 407 may add an elution buffer to the reaction vessel containing the processed sample. The reagent pipetting station may then mix the elution buffer with the magnetic particles including the bound analyte. After this step has been performed, the second pick and place gripper 409 may then transfer the reaction vessel to the incubator in the incubator/wash/read station 412.

In step 814, in the incubator, an incubation process may be performed in the incubator in the incubator/wash/read station 412. The mixture in the reaction vessel may be incubated for any suitable period of time.

In step 816, a magnetic separation process can be performed in a wash station in the incubator/wash/read station 412 to separate the supernatant from the magnetic particles. Alternatively, as noted above, a magnetic separation process can be performed in the incubator in the incubator/wash/read station 412 if the incubator includes incubation regions with magnets. In other case, a magnet in either the wash station or the incubator in the incubator/wash/read station 412, or even in one of the pipetting stations 404, 405, 406, 407 may confine the magnetic particles to a location in the reaction vessel.

In step S822, the supernatant containing the analyte of interest in the reaction vessel may be transferred to a second reaction vessel using pipettor proximate to the incubator/wash/read station, or at any other suitable location, leaving behind the magnetic particles in the first reaction vessel.

In step 824, the second reaction vessel or the supernatant containing the analyte of interest may be transferred to the mass spectrometer using one or more of sample introduction apparatuses.

If desired, at this point in the process, one or more mass tags or derivativing agents may be added to the supernatant containing the analyte of interest. The mass tags or derivatizing agent can be added by one of more of the reagent pipetting stations 404, 405, 406, 407.

In step 826, once the supernatant containing the analyte of interest is in the mass spectrometer, a mass analysis can be performed.

In step 828, a data analysis may be performed by the mass spectrometer, as described above.

FIG. 9 shows a flowchart illustrating a protein precipitation process according to an embodiment of the invention. In a protein precipitation process, proteins in a sample that are not of interest can be bound to magnetic particles. The magnetic particles may be separated from a supernatant containing the analyte of interest in a reaction vessel. The analysis illustrated in FIG. 9 can be performed instead of an immunoassay process or as a reflex test for a prior immunoassay process.

In step 902, a sample in a sample tube is loaded into the sample presentation unit 401 in the analyzer 400. The sample tube may be present along with a number of other sample tubes in a sample tube rack or other sample tube carrier.

In step 904, the main sample pipetting station 402 may then pipette a mixture of an aliquot of the sample, assay standard, and precipitation buffer containing paramagnetic microparticles into the reaction vessel provided by the bulk vessel feeder 403. The mixture in the reaction vessel may then be mixed at the main sample pipetting station using multiple dispense and aspiration steps, or using any other suitable mixing process.

At this point, the second pick and place gripper 409 may transfer the reaction vessel to the incubator/wash/read station 412.

In step 906, in the incubator in the incubator/wash/read station 412, the reaction vessel containing the mixture may be incubated, so that any protein matrix within the sample aliquot is bound to the paramagnetic microparticles.

In step 908, in the wash apparatus in the incubator/wash/read station 412, the paramagnetic microparticles with the bound protein matrix magnetically separated from the supernatant containing the analyste of interest. Alternatively, as noted above, a magnetic separation process can be performed in the incubator in the incubator/wash/read station 412 if the incubator includes incubation regions with magnets.

In step 910, the supernatant containing the analyte of interest in the reaction vessel may be transferred to a second reaction vessel provided by the bulk vessel feeder 403 using a pipettor proximate to the incubator/wash/read station 412.

In step 914, once the supernatant containing the analyte of interest is in the mass spectrometer, a mass analysis can be performed.

In step 916, a data analysis may be performed by the mass spectrometer.

In some embodiments, instead of performing steps 908, 910, and 912, the analyzer could transfer the reaction vessel to a centrifuge module (which may be located in the analyzer, the mass spectrometer, or may be separate from them), spun, and then returned to the analyzer.

FIG. 10 shows a flowchart illustrating another immunopurification process according to an embodiment of the invention. The process illustrated in FIG. 10 may be a SISCAPA-type processing method as described above.

In step 1002, a sample in a sample tube is loaded into the sample presentation unit 401 in the analyzer 400. The sample tube may be present along with a number of other sample tubes in a sample tube rack or other sample tube carrier.

In step 1004, the main sample pipetting station 402 may then pipette an aliquot of the sample in the sample tube, and a denaturing reagent/alkenylating reagent, into a reaction vessel provided by the bulk vessel feeder 403. The first pick and place gripper 408 may then transfer the reaction vessel to the incubator in the incubator/wash/read station 412 so that an incubation process can be performed.

In step 1006, the reaction vessel containing the sample is incubated.

After incubation, the second pick and place gripper 409 may transfer the reaction vessel to the reagent pipetting stations 404, 405, 406, 407.

In step 1008, one of the reagent pipetting stations 404, 405, 406, 407 may add trypsin and may mix the resulting mixture in the reaction vessel. The second pick and place gripper 409 may then transfer the reaction vessel to the incubator in the incubator/wash/read station 412.

In step 1010, in the incubator, an incubation process may be performed in the incubator of the incubator/wash/read station 412. At this point, the second pick and place gripper 409 may transfer the reaction vessel to one of the reagent pipetting stations 404, 405, 406, 407.

In step 1012, one of the reagent pipetting stations 404, 405, 406, 407 may add magnetic microparticles coated with antibodies and SIS peptides. After this step has been performed, the second pick and place gripper 409 may then transfer the reaction vessel to the incubator in the incubator/wash/read station 412.

In step 1014, in the wash apparatus in the incubator/wash/read station 412, a magnetic separation and wash process may be performed. Once this process step has been performed, the second pick and place gripper 409 may then transport the reaction vessel to the reagent pipetting stations 404, 405, 406, 407.

In step 1016, one of the reagent pipetting stations 404, 405, 406, 407 may add an elution buffer and may then mix the elution buffer with the magnetic particles including the bound analyte. After this step has been performed, the second pick and place gripper 409 may then transfer the reaction vessel to the incubator in the incubator/wash/read station 412.

In step 1018, in the incubator, an incubation process may be performed in the incubator in the incubator/wash/read station 412.

In step 1020, a magnetic separation process can be performed in a wash station in the incubator/wash/read station 412. Alternatively, as noted above, a magnetic separation process can be performed in the incubator in the incubator/wash/read station 412 if the incubator includes incubation regions with magnets.

In step 1022, the supernatant containing the analyte of interest in the reaction vessel may be transferred to a second reaction vessel using pipettor proximate to the incubator/wash/read station.

In step 1024, the second reaction vessel or the supernatant containing the analyte of interest may be transferred to the mass spectrometer using one or more sample introduction apparatuses.

In step 1026, once the supernatant containing the analyte of interest is in the mass spectrometer, a mass analysis can be performed.

In step 1028, a data analysis may be performed by the mass spectrometer.

The integrated sample processing system according to embodiments of the invention can be used to measure or determine the presence of a variety of analytes, such as hormones, drugs of abuse, and tumor markers in one or more samples.

Non-limiting examples of drugs of abuse that can be measured include amphetamine, barbiturates, benzodiazepines, opiates, oxycodone, cocaine, methadone, EDDP, THC, and buprenorphine. Samples for drug tests are typically urine or oral fluid, such as saliva. In some embodiments, the samples are first measured in an analyzer such as a chemistry analyzer or an immunoanalyzer to produce measurement results. The results are then input into the control system, which compares the results with one or more predetermined assay thresholds. If the measurement results exceed (e.g., are greater than) the one or more thresholds, the control system can determine that samples contain the drug of interest. If the measurement results do not exceed the one or more thresholds, then the control system can determine that the specimens do not contain the drug. In some embodiments, if the results from the analyzer are positive for the particular drug, the control system then orders a second aliquot of sample to be taken and a confirmatory test by the mass spectrometer (MS). When the one or more drugs are drugs of above, criteria specified in the Mandatory Guidelines for Federal Workplace Drug Testing Program issued by the Substance Abuse and Mental Health Services Administration (SAMHSA) Federal Register, 82 FR Vol. 82, 7920, 7942 (2017) can be used Non-limiting examples of hormones that can be analyzed in samples can include aldosterone, plasma renin aitivty, cortisone, corticosterone, progesterone, cortisol, androstenedione, methylmalonic acid, homocystine, progesterone, DHEAS, estradiol/17-beta-estradiol, estrone, testosterone, 11-deoxycortisol, 17-hydroxyprogesterone, pregnenolone, and 17-hydroxypregnenolone. In some embodiments, the levels of certain hormones can differ significantly depending on gender and age. For example, the amount of testosterone is 10 fold higher in males than in females. Since an immunoanalyzer is typically limited in sensitivity as compared to mass spectrometry, for certain demographic groups in which the target hormone is known to be low, these hormones can be directly be tested in the mass spectrometer. In some embodiments, when the demographic information of the patient is not available, typically, the analyzer such as the immunoanalyzer can used as an initial test. Samples that are shown to have very low levels of the target hormone (e.g., being lower than a predetermined threshold, at which the immunoanalyzer cannot accurately measure the concentration), the control system can order a reflex test by the mass spectrometer to accurately measure the concentration of the target hormone in the sample.

Non-limiting examples of tumor markers that can be measured using the integrated sample processing system disclosed herein include lipase, alpha-feto protein, CA 125, CA 15-3, CA19-9, CA 27-29, CEA, beta hCG+hCG, parathyroid hormone. In some embodiments, the panel can include 10-500, e.g., 20-100, 30-400, or 50-200 known tumor markers. For assaying large panels of analytes, such as tumor markers, mass spectrometry is first used as a screening assay to identify a subset of markers that are positive for the sample, and the chemistry/immune analyzer is then used to confirm that these markers are positive. Since the mass spectrometer can be particularly suited for multiplex testing but may not be a government (e.g., FDA) approved diagnostic method, and because an immunoassay test can be a government (e.g., FDA) approved test but may be less expensive to run that mass spectrometry, the combination of these two techniques provides the unique advantage of rapid marker identification and certification.

EXAMPLES

Exemplary Sample Collection Methods

The integrated sample processing system disclosed herein can be used to measure analytes from a variety of bodily fluids, such as serum, plasma, and urine. The descriptions below include details of some sample collection method and are illustrative and not restrictive.

Serum samples can be prepared from whole blood drawn from a subject. The blood sample can be left undisturbed at room temperature for 15-30 minutes to allow it to clot. The sample is then centrifuged for at least 15 minutes at 1,000-2,000 g in a refrigerated centrifuge. The supernatant, which is the serum, can be immediately transferred to a clean vial with a sterile pipette. The serum sample can be kept at 2-8° C. while handling. If the serum is not analyzed immediately, the serum can be stored at −20° C. or lower until use. Repeated freeze-thaw cycles can be avoided as this can be detrimental to many serum components and could affect the accuracy of the assay.

Plasma samples can be also be prepared from the whole blood sample from a subject. The whole blood can be drawn and collected into tubes treated with anticoagulant e.g., heparin. Cells can be removed from plasma by centrifugation for 10 minutes at 1,000-2,000×g using a refrigerated centrifuge. The resulting supernatant, which is plasma, can be immediately transferred into a clean vial with a sterile pipette. The handling and storage of the plasma samples can be the same as serum samples, as described above.

Urine samples can be collected according to the SAMHSA guidelines (Substance Abuse and Mental Health Services Administration Center for Substance Abuse Prevention), available at https://www.samhsa.gov/sites/default/files/specimen-collection-handbook-2014.pdf.

Example 1: Testosterone

The sample processing system according to embodiments of the invention can be used to measure testosterone in biofluid samples. Testosterone in males is secreted by adult Leydig cells and is controlled by lutenizing hormone (LH). An abnormally low total testosterone level in males can be indicative of hypogonadism, hypopituitarism, hyperprolactinemia, renal failure, hepatic cirrhosis, or Kleinfelter's syndrome. High total testosterone values in males can be caused by adrenal and testicular tumors, congenital adrenal hyperplasia or abnormalities of the hypothalamic-pituitary-testicular axis. In females, testosterone is produced in the ovaries, adrenal gland, and peripheral fatty tissues. Increased female total testosterone levels may indicate polycystic ovary syndrome (PCOS), stromal hyperthecosis, ovarian and adrenal tumors, congenital adrenal hyperplasia and other disorders of the hypothalamic-pituitary-ovarian axis. Thus, there is a need to monitor testosterone levels in both males and females. Since females typically have a serum concentration that is approximately 10-fold less than in males, and the immunoanalyzer is often not sensitive enough to reliably measure the very low levels of testosterone, MS is often the preferred method for measuring testosterone in females. However, in some instances, the demographic information (e.g., the gender of the subject) is not available at the time of the testing. Thus, in some embodiments, an initial test is performed by the immunoanalyzer. If the immunoanalyzer indicates a low testosterone level in a particular sample that is below the detection range, the control system can then order a confirmatory test using the MS.

An Access Testosterone assay kit (commercially available from Beckman Coulter, Inc., Brea, CA) can be used for the initial testing for testosterone in a biological sample. The assay can be run on the immunoanalyzer of the sample processing system. The Access Testosterone assay is a competitive binding immunoenzymatic assay, using a mouse monoclonal anti-testosterone antibody, a testosterone alkaline phosphatase conjugate, and paramagnetic particles coated with a goat anti-mouse polyclonal antibody. Testosterone in the sample is released from the carrier proteins and competes with the testosterone alkaline phosphatase conjugate for binding sites on a limited amount of specific anti-testosterone monoclonal antibodies. The resulting antigen-antibody complexes are then bound to the solid phase by the capture antibody. After incubation in a reaction vessel, materials bound to the solid phase are held in a magnetic field while unbound materials are washed away.

Then, the chemiluminescent substrate Lumi-Phos* 530 is added to the vessel and light generated by the reaction is measured with a luminometer. The light production is inversely proportional to the concentration of testosterone in the sample. The amount of the analyte in the sample is determined from a stored, multi-point calibration curve.

In a first test, a serum sample is obtained from a first subject, for whom no demographic information (age, gender etc.) is available, is loaded onto the system sample preparation module in the immunoanalyzer and is prepared using the Access Testosterone assay kit described above. The immunoassay is run on the immunoanalyzer. The results of immunoassay, which may include a serum testosterone amount, are sent to a control system in the immunoanalyzer which compares the measurements with the reference range for serum testosterone, i.e., the range of concentrations in healthy individuals. For males between ages 18-66, the reference serum testosterone level is typically 1.75-7.81 ng/mL and for females, the reference serum testosterone level is typically less than 0.1-0.75 ng/mL. An attending physician may determine a threshold above which the results from the immunoanalyzer are deemed accurate. If the patient has an amount of testosterone that is below the threshold, the control system in the immunoanalyzer can then cause a second aliquot from the sample to be prepared as described above. The threshold value may vary, depending on the level of precision and accuracy required for the test, but it is typically a value within the range of 2-0.1 ng/mL, e.g., 1.75 ng/mL or 0.8 ng/mL. The second aliquot of the sample may then be processed (as described above). The processed sample is then transferred to the mass spectrometer in the sample processing system and is injected into the mass spectrometer. The mass spectrometer then determines the testosterone amount or concentration in the serum sample. The results of the tests performed by the immunoanalyzer and the mass spectrometer can then be reported.

In a second exemplary test, a serum sample can obtained from a second subject. The medical record for the second subject can be accessible and can indicate that the subject is a female. This information can be sent to the control system in the sample processing system, which determines that the sample is to be analyzed by only the mass spectrometer, and does not need to be analyzed by the immunoanalyzer. The control system then causes an aliquot of sample to be prepared and processed. The processed sample aliquot is then injected into the mass spectrometer as described above. The mass spectrometer then measures the testosterone amount in the serum sample of the second subject. The measurements from the mass spectrometer are then reported.

Example 2: Amphetamines

The sample processing system according to embodiments of the invention can be used to test for drugs of abuse. One exemplary drug of abuse type is amphetamines. Amphetamines are central nervous system stimulants that produce wakefulness, alertness, increased energy, reduced hunger, and overall feeling of well-being.

Amphetamines appear in urine within three hours after any type of administration and can be detected by this Emit® II plus amphetamines assay (commercially available from Beckman Coulter, Inc., Brea, CA) for as long as 24-48 hours after the last dose. The Emit® II plus amphetamines assay is a homogeneous enzyme immunoassay. The assay is based on a competition between a drug in the specimen and a drug labeled with the enzyme glucose-6-phosphate dehydrogenase (G6PDH) for antibody binding sites. Enzyme activity decreases upon binding to the antibody, so the drug concentration in the specimen can be measured in terms of enzyme activity. Active enzymes convert nicotinamide adenine dinucleotide (NAD) to NADH, resulting in an absorbance change that is measured spectrophotometrically. Endogenous serum G6PDH does not interfere because the coenzyme NAD functions only with the bacterial (*Leuconostoc mesenteroides*) enzyme employed in the assay.

The reagents used in the test can include mouse monoclonal antibodies to d-amphetamine (61 μg/mL) and d-methamphetamine (10 μg/mL), glucose-6-phosphate (5.5 mM), nicotinamide adenine dinucleotide (3.5 mM), bovine serum albumin, amphetamines labeled with bacterial G6PDH (0.72 U/mL), Tris buffer, preservatives and stabilizers.

For the drug test, urine samples can be collected according to the SAMHSA guidelines (Substance Abuse and Mental Health Services Administration Center for Substance Abuse Prevention), available at https://www.samhsa.gov/sites/default/files/specimen-collection-handbook-2014.pdf. Urine specimen are typically submitted to certified laboratories within 24 hours after collection. Urine samples are prepared in a sample preparation module in the sample processing system. The reagents are added to the sample to be tested and an immunoassay is performed on the immunoanalyzer. The results are then input into the control system in the sample processing system. The control system then compares the results with an assay threshold. For example, if the amount is greater than the threshold, e.g., 300 ng/mL, the control system determines that, as a preliminary reading, the sample contains amphetamines. If the amount is lower than the threshold, the control system determines that specimens do not contain amphetamines.

If the results from the analyzer are positive, the control system then orders a confirmatory test to be performed by the mass spectrometer. A second aliquot of sample is then taken and prepared for the mass spectrometer as described above. Calibration standards and controls that contain amphetamines are purchased from Cerilliant, Inc. and Utak Laboratories, Inc. If the mass spectrometry measurements indicate that the second processed sample aliquot contains amphetamines, then the subject is identified as positive for amphetamines and a report will be generated.

Example 3 Tumor Marker Panel

The integrated sample processing system can also be used for cancer diagnosis. Mass spectrometry is useful for multiplex testing and thus can be used to test a large panel of tumor antigens such as a panel with hundreds of known tumor markers. In one example, the tumor panel include lipase, alpha-feto protein, CA125, CA15-3, CA19-9, CA27-29, CEA, Beta hCG+hCG, parathyroid hormone. However, mass spectrometry may not be a governmental approved diagnostic method in some jurisdictions. In such cases, a confirmatory test can be run by the immunoanalyzer in the sample processing system to confirm the initial determination made by the mass spectrometer.

To test a tumor panel, plasma samples are prepared as described above. A first aliquot of the plasma sample is prepared as described above and is sent to the mass spectrometer. The results are returned to the control system in the sample processing system, which compares the measurements with predetermined thresholds to determine if any of the tumor markers is positive in the sample (i.e., the measurement(s) is above the threshold(s) for the particular marker(s)).

If a small subset of the tumor markers is indicated as being positive according to the mass spectrometer data, the control system in the sample processing system then instructs the sample preparation module in the immunoanalyzer to prepare and process a second aliquot of sample. The immunoanalyzer then detects the subset of tumor markers using a multiplex, fluorescence-based sandwich immunoassay. The assay can involve adding to the sample aliquot primary antibodies that are specific to respective tumor markers in the subset and detection antibodies that are conjugated to fluorophores and can recognize each of the primary antibodies. The fluorophores have different excitation and emission wavelengths, so that fluorescent signals from the detection antibodies will not interfere with one another. The fluorescent signal from each of the detection antibodies is measured, which represents the amount of each of the corresponding tumor markers in the sample. The results of the tumor markers that are determined to be positive by the immunoanalyzer are then reported.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

All patents, patent applications, publications, and descriptions mentioned above are herein incorporated by reference in their entirety.

What is claimed is:

1. A method performed by a sample processing system comprising an analyzer, a mass spectrometer, a sample introduction apparatus, and a control system, the control system operatively coupled to the analyzer, the mass spectrometer, and the sample introduction apparatus, the method comprising:
    performing, by the analyzer, a primary analysis of an analyte in a first processed sample aliquot derived from a first sample aliquot of a sample in a reaction vessel;
    determining, whether a concentration of analyte in the first processed sample aliquot is below, above, or equal to a predetermined threshold;
    transferring, by the sample introduction apparatus, a second processed sample aliquot derived from a second sample aliquot of the sample from the analyzer to the mass spectrometer; and
    performing, by the mass spectrometer, a secondary analysis of the analyte or another analyte in the second processed sample aliquot in a secondary analysis.

2. The method of claim 1, wherein the analyzer comprises two or more of: a pipetting station, a reagent dispensing station, an incubator, and a washing and separation station.

3. The method of claim 1, wherein the analyzer is an immunoanalyzer.

4. The method of claim 1, wherein processing the first sample aliquot comprises:
    dispensing reagents into a reaction vessel containing the first sample aliquot;
    incubating, the reaction vessel containing the reagents and the sample aliquot; and
    separating, the analyte from the other components in the first sample aliquot using a washing and magnetic separation process.

5. A method performed by a sample processing system comprising at least a mass spectrometer, a sample introduction apparatus, and a control system, the control system operatively coupled to the mass spectrometer and the sample introduction apparatus, the method comprising:
    performing, by the mass spectrometer, a primary analysis of an analyte from a first processed sample aliquot of a first sample aliquot of the sample; and
    after performing the primary analysis, performing, by the mass spectrometer or an analyzer in the sample processing system, a secondary analysis of the analyte or another analyte in a second processed sample aliquot derived from a second aliquot of the sample.

6. The method of claim 5, wherein the sample processing system further comprises an analyzer comprising an immunoanalyzer.

7. The method of claim 5, wherein the analyte or the another analyte comprises a steroid or a drug of abuse.

8. The method of claim 5, wherein the sample processing system further comprises an analyzer, wherein the analyzer comprises an aliquoting station.

9. The method of claim 5, wherein the analyte is one of many analytes in a panel of analytes that are capable of being identified in the first processed sample aliquot in the first analysis.

10. The method of claim 5, wherein the sample processing system further comprises the analyzer, and the secondary analysis is performed by the analyzer.

11. The method of claim 5, wherein the secondary analysis is performed by the mass spectrometer.

12. A sample processing system comprising:
    a mass spectrometer;
    a sample introduction apparatus; and
    a control system, wherein the control system controls operation of the mass spectrometer and the sample introduction apparatus, and wherein the control system comprises a processor, and a computer readable medium, the computer readable medium comprising code, executable by the processor, for implementing a method comprising:
    performing, by the mass spectrometer, a primary analysis of an analyte from a first processed sample aliquot of a first sample aliquot of the sample, and
    after performing the primary analysis, performing, by the mass spectrometer or an analyzer in the sample processing system, a secondary analysis of the analyte or another analyte in a second processed sample aliquot derived from a second aliquot of the sample.

13. The sample processing system of claim 12, wherein the sample processing system further comprises the analyzer, wherein the analyzer is an immunoanalyzer or a chemistry analyzer.

14. The sample processing system of claim 13, wherein the analyzer comprises an aliquoting station.

15. The sample processing system of claim 13, wherein the analyzer comprises reagents for performing a mass spectrometric analysis and reagents for performing an immunoassay analysis.

16. The sample processing system of claim 13, wherein the sample introduction apparatus is configured to provide a processed sample aliquot from the analyzer to the mass spectrometer.

17. The sample processing system of claim 12, wherein the analyte is one of many analytes in a panel of analytes that are capable of being identified in the first processed sample aliquot in the first analysis.

18. The sample processing system of claim 12, further comprising the analyzer, wherein the secondary analysis is performed by the analyzer.

19. The sample processing system of claim 12, wherein the secondary analysis is performed by the mass spectrometer.

* * * * *